US010736320B2

United States Patent
Edmunds et al.

(10) Patent No.: US 10,736,320 B2
(45) Date of Patent: Aug. 11, 2020

(54) PESTICIDALLY ACTIVE POLYCYCLIC DERIVATIVES WITH 5-MEMBERED SULFUR CONTAINING HETEROCYCLIC RING SYSTEMS

(71) Applicant: Syngenta Participations AG, Basel (CH)

(72) Inventors: Andrew Edmunds, Stein (CH); Michel Muehlebach, Stein (CH); Pierre Joseph Marcel Jung, Stein (CH); Daniel Emery, Stein (CH); Anke Buchholz, Stein (CH); Ruifang Chen, Shanghai (CN); Long Lu, Shanghai (CN); Yaming Wu, Shanghai (CN)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/762,994

(22) PCT Filed: Sep. 19, 2016

(86) PCT No.: PCT/EP2016/072141
§ 371 (c)(1),
(2) Date: Mar. 23, 2018

(87) PCT Pub. No.: WO2017/050685
PCT Pub. Date: Mar. 30, 2017

(65) Prior Publication Data
US 2018/0213784 A1  Aug. 2, 2018

(30) Foreign Application Priority Data

Sep. 25, 2015 (WO) ................ PCT/CN2015/090700

(51) Int. Cl.
| | | |
|---|---|---|
| *A01N 43/82* | (2006.01) | |
| *C07D 417/04* | (2006.01) | |
| *C07D 417/14* | (2006.01) | |
| *A01N 43/78* | (2006.01) | |

(52) U.S. Cl.
CPC ............. *A01N 43/82* (2013.01); *A01N 43/78* (2013.01); *C07D 417/04* (2013.01); *C07D 417/14* (2013.01)

(58) Field of Classification Search
CPC .. C07D 417/04; C07D 417/14; C07D 277/22; C07D 285/12; C07D 277/20; A01N 43/82; A01N 43/78
See application file for complete search history.

(56) References Cited

U.S. PATENT DOCUMENTS

| 4,245,432 A * | 1/1981 | Dannelly ................ A01C 1/06 47/57.6 |
|---|---|---|
| 2011/0212949 A1* | 9/2011 | Bretschneider ........ A01N 43/56 514/229.2 |
| 2017/0190696 A1* | 7/2017 | Orimoto ............ C07D 413/14 |

FOREIGN PATENT DOCUMENTS

| CN | 102159079 A | 8/2011 |
|---|---|---|
| EP | 3135114 A1 | 3/2017 |
| JP | 2008308448 A | 12/2008 |
| WO | 2012086848 A1 | 6/2012 |
| WO | 2013018928 A1 | 2/2013 |
| WO | 2014125651 A1 | 8/2014 |
| WO | 2015144826 A1 | 10/2015 |
| WO | 2015144895 A1 | 10/2015 |
| WO | 2015163478 A1 | 10/2015 |

OTHER PUBLICATIONS

International Search Report and Written Opinion for PCT/CN2015/090700, dated Jan. 11, 2016.
International Search Report and Written Opinion for PCT/EP2016/072141, dated Oct. 31, 2016.

* cited by examiner

*Primary Examiner* — John Pak
(74) *Attorney, Agent, or Firm* — Baker & Hostetler, LLP; Toni-Junell Herbert

(57) ABSTRACT

Pesticidally active polycyclic derivatives with 5-membered sulfur containing heterocyclic ring systems of formula (I), wherein the substituents are as defined in claim 1, and the agrochemically acceptable salts salts, stereoisomers, enantiomers, tautomers and N-oxides of those compounds, can be used as insecticides and can be prepared in a manner known per se.

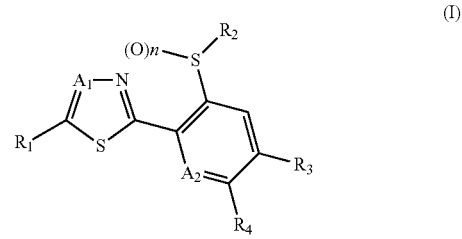

16 Claims, No Drawings

PESTICIDALLY ACTIVE POLYCYCLIC DERIVATIVES WITH 5-MEMBERED SULFUR CONTAINING HETEROCYCLIC RING SYSTEMS

CROSS-REFERENCE TO RELATED APPLICATIONS

This application is a 371 National Stage application of International Application No. PCT/EP2016/072141, filed Sep. 19, 2016, which claims priority to International Patent Application No. PCT/CN2015/090700, filed Sep. 25, 2015, the entire contents of which are hereby incorporated by reference.

The present invention relates to pesticidally active, in particular insecticidally active polycyclic derivatives with 5-membered sulfur containing heterocyclic ring systems to compositions comprising those compounds, and to their use for controlling animal pests, including arthropods and in particular insects or representatives of the order Acarina.

Heterocyclic compounds with pesticidal action are known and described, for example, in WO 2012/086848, WO 2013/018928 and WO 2015/000715. There have now been found novel pesticidally active polycyclic ring derivatives with sulfur containing five-membered ring substituted heterocyles.

The present invention accordingly relates to compounds of formula I,

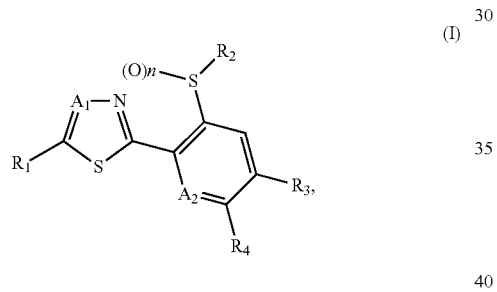

(I)

wherein
$A_1$ and $A_2$ is methine or N;
$R_2$ is $C_1$-$C_4$ alkyl, $C_3$-$C_4$ cycloalkyl, or $C_1$-$C_4$ alkyl-$C_3$-$C_4$-cycloalkyl
n is 0, 1 or 2;
$R_1$ is selected from a group consisting of $J_0$ to $J_{30}$

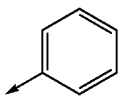
J-0

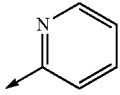
J-1

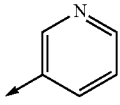
J-2

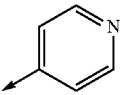
J-3

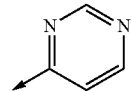
J-4

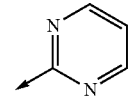
J-5

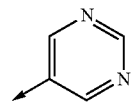
J-6

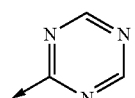
J-7

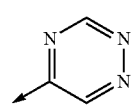
J-8

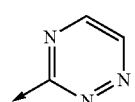
J-9

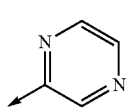
J-10

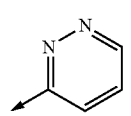
J-11

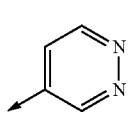
J-12

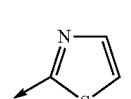
J-13

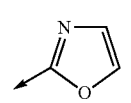
J-14

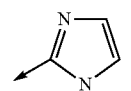
J-15

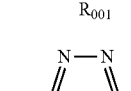
J-16

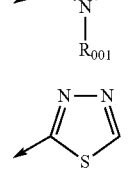
J-17

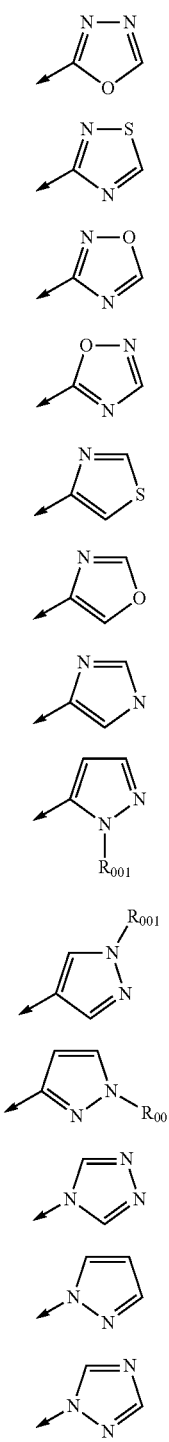

wherein the arrow represents the point of attachment to formula I, and each of the groups $J_0$ to $J_{30}$ can be mono- di- or trisubstituted by a group Rx, wherein Rx is independently selected from the group consisting of hydrogen, halogen, cyano, $C_1$-$C_4$ alkyl, $C_1$-$C_4$ haloalkyl, $C_1$-$C_4$ haloalkoxy, $C_1$-$C_4$ alkoxy, $C_1$-$C_4$ alkylsulfanyl, $C_1$-$C_4$ alkylsulfinyl, $C_1$-$C_4$ alkylsulfonyl, —C(O)$C_1$-$C_4$ alkyl, —C(O)$C_1$-$C_4$ haloalkyl, $C_1$-$C_4$ haloalkylsulfanyl, $C_1$-$C_4$ haloalkylsulfinyl and $C_1$-$C_4$ haloalkylsulfonyl, and wherein $R_{001}$ represents hydrogen or $C_1$-$C_4$ alkyl;

$R_3$ and $R_4$, independently from each other, are hydrogen, halogen, $C_1$-$C_4$ haloalkoxy, $C_1$-$C_4$ haloalky, amino, hydroxy or cyano; or $R_3$ and $R_4$, independently from each other, are phenyl which can be mono- or polysubstituted by substituents selected from the group consisting of halogen, cyano, $C_1$-$C_4$ alkyl, $C_1$-$C_4$ haloalkyl, $C_1$-$C_4$ haloalkoxy, $C_1$-$C_4$ alkoxy, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; or $R_3$ and $R_4$, independently from each other, are a five- to ten-membered monocyclic or fused bicyclic ring system linked via a carbon atom to the ring which contains the group $A_2$, said ring system can be aromatic, partially saturated or fully saturated and contains 1 to 4 hetero atoms selected from the group consisting of nitrogen, oxygen and sulfur, with the proviso that each ring system cannot contain more than 2 oxygen atoms and more than 2 sulfur atoms, said five- to ten-membered ring system can be mono- to polysubstituted by substituents independently selected from the group consisting of halogen, cyano, $C_1$-$C_4$ alkyl, $C_1$-$C_4$ haloalkyl, $C_1$-$C_4$ haloalkoxy, $C_1$-$C_4$ alkoxy, $C_1$-$C_4$ alkylsulfanyl, $C_1$-$C_4$ alkylsulfinyl, $C_1$-$C_4$ alkylsulfonyl, —C(O)$C_1$-$C_4$ alkyl, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; or $R_3$ and $R_4$, independently from each other, are a five- to six-membered, aromatic, partially saturated or fully saturated ring system linked via a nitrogen atom to the ring which contains the group $A_2$, said ring system can be mono- or polysubstituted by substituents selected from the group consisting of halogen, cyano, $C_1$-$C_4$ alkyl, $C_1$-$C_4$ haloalkyl, $C_1$-$C_4$ haloalkoxy, $C_1$-$C_4$ alkoxy, $C_1$-$C_4$ alkylsulfanyl, $C_1$-$C_4$ alkylsulfinyl, $C_1$-$C_4$ alkylsulfonyl, —C(O)$C_1$-$C_4$ alkyl, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; and said ring system contains 1, 2 or 3 heteroatoms selected from the group consisting of nitrogen, oxygen and sulfur, with the proviso that said ring system cannot contain more than one oxygen atom and more than one sulfur atom; or $R_3$ and $R_4$, independently from each other, are $C_3$-$C_6$ cycloalkyl, or $C_3$-$C_6$ cycloalkyl mono- or polysubstituted by substituents selected from the group consisting of halogen, cyano, $C_1$-$C_4$ alkyl, $C_1$-$C_4$ haloalkyl, $C_3$-$C_6$ cycloalkyl and phenyl, wherein said phenyl can be mono- or polysubstituted by substituents selected from the group consisting of halogen, cyano, $C_1$-$C_4$ alkyl, $C_1$-$C_4$ haloalkyl, $C_1$-$C_4$ haloalkoxy, $C_1$-$C_4$ alkoxy, $C_1$-$C_4$ haloalkylsulfanyl, $C_1$-$C_4$ halo-alkylsulfinyl, $C_1$-$C_4$ haloalkylsulfonyl and —C(O)$C_1$-$C_4$ haloalkyl; or $R_3$ and $R_4$, independently from each other, are $C_2$-$C_6$ alkenyl, or $C_2$-$C_6$ alkenyl mono- or polysubstituted by substituents selected from the group consisting of halogen, cyano, $C_1$-$C_4$ alkyl, $C_1$-$C_4$ haloalkyl, $C_3$-$C_6$ cycloalkyl and phenyl, wherein said phenyl can be mono- or polysubstituted by substituents selected from the group consisting of halogen, cyano, $C_1$-$C_4$ alkyl, $C_1$-$C_4$ haloalkyl, $C_1$-$C_4$ haloalkoxy, $C_1$-$C_4$ alkoxy, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; or $R_3$ and $R_4$, independently from each other, are $C_2$-$C_6$ alkynyl or $C_2$-$C_6$ alkynyl; or are $C_2$-$C_6$ alkynyl or $C_2$-$C_6$ alkynyl mono- or polysubstituted by substituents selected from the group consisting of halogen, cyano, $C_1$-$C_4$ alkyl, $C_1$-$C_4$ haloalkyl, $C_3$-$C_6$ cycloalkyl, tri($C_1$-$C_4$ alkyl) silyl and phenyl, wherein said phenyl can be mono- or polysubstituted by substituents selected from the group consisting of halogen, cyano, $C_1$-$C_4$ alkyl, $C_1$-$C_4$ haloalkyl, $C_1$-$C_4$ haloalkoxy, $C_1$-$C_4$ alkoxy, $C_1$-$C_4$ halo-alkylsulfanyl, $C_1$-$C_4$ haloalkylsulfinyl, $C_1$-$C_4$ haloalkylsulfonyl and —C(O)$C_1$-$C_4$ haloalkyl; or $R_3$ and $R_4$, independently from each other, are $C_1$-$C_6$ alkyl, or $C_1$-$C_6$ alkyl mono- or polysubstituted by substituents selected from the group consisting of halogen, cyano, $C_1$-$C_4$ alkyl, $C_1$-$C_4$ haloalkyl, $C_3$-$C_6$ cycloalkyl, tri($C_1$-$C_4$ alkyl)silyl and phenyl, wherein said phenyl can be mono- or polysubstituted by substituents selected from the group consisting of halogen, cyano, $C_1$-$C_4$ alkyl, $C_1$-$C_4$ haloalkyl, $C_1$-$C_4$ haloalkoxy, $C_1$-$C_4$ alkoxy, $C_1$-$C_4$ halo-alkylsulfanyl, $C_1$-$C_4$ haloalkylsulfinyl, $C_1$-$C_4$ haloalkylsulfonyl and —C(O)$C_1$-$C_4$ haloalkyl; and agrochemically acceptable salts, stereoisomers, enantiomers, tautomers of the compounds of formula I.

Compounds of formula I which have at least one basic centre can form, for example, acid addition salts, for example with strong inorganic acids such as mineral acids, for example perchloric acid, sulfuric acid, nitric acid, a phosphorus acid or a hydrohalic acid, with strong organic carboxylic acids, such as $C_1$-$C_4$ alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$ alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated. $C_1$-di-alkylamino is dimethylamino.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl.

Alkoxy is, for example, methoxy, ethoxy, propoxy, i-propoxy, n-butoxy, isobutoxy, sec-butoxy and tert-butoxy and also the isomeric pentyloxy and hexyloxy radicals.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkoxycarbonyl is for example methoxycarbonyl (which is $C_1$ alkoxycarbonyl), ethoxycarbonyl, propoxycarbonyl, isopropoxycarbonyl, n-butoxycarbonyl, tert-butoxycarbonyl, n-pentoxycarbonyl or hexoxycarbonyl.

Alkylsulfanyl is for example methylsulfanyl, ethylsulfanyl, propylsulfanyl, isopropylsulfanyl, butylsulfanyl, pentylsulfanyl, and hexylsulfanyl.

Alkylsulfinyl is for example methylsulfinyl, ethylsulfinyl, propylsulfinyl, isopropylsulfinyl, a butylsulfinyl, pentylsulfinyl, and hexylsulfinyl.

Alkylsulfonyl is for example methylsulfonyl, ethylsulfonyl, propylsulfonyl, isopropylsulfonyl, butylsulfonyl, pentylsulfonyl, and hexylsulfonyl.

Haloalkylsulfanyl is for example trifluoromethylsulfanyl, 2,2,2-trifluoroethylsulfanyl, and pentafluoroethylsulfanyl.

Haloalkylsulfinyl is for example trifluoromethylsulfinyl, 2,2,2-trifluoroethylsulfinyl, or pentafluoroethylsulfinyl.

Haloalkylsulfonyl is for example trifluoromethylsulfonyl, 2,2,2-trifluoroethylsulfonyl, and pentafluoroethylsulfonyl.

Cycloalkyl is, for example, cyclopropyl, cyclobutyl, cyclopentyl and cyclohexyl.

In the context of this invention, examples of a five- to six-membered, aromatic, partially saturated or fully saturated ring system that are linked via a nitrogen atom to the 5-memebered heterocyclic ring, are for example, pyrazole, pyrrole, pyrrolidine, pyrrolidine-2-one, piperidine, morpholine, imidazole, triazole and pyridine-2-one.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, double- or triple-substituted.

The compounds of formula I according to the invention also include hydrates which may be formed during the salt formation.

According to the present invention, a five- to ten-membered monocyclic or fused bicyclic hetero-ring system which can be aromatic, partially saturated or fully saturated and contains 1 to 4 hetero atoms selected from the group consisting of nitrogen, oxygen and sulfur, with the proviso that each ring system cannot contain more than 2 oxygen atoms and more than 2 sulfur atoms or a three- to ten-membered, monocyclic or fused bicyclic ring system which may be aromatic, partially saturated or fully saturated is, depending of the number of ring members, preferably selected from the group consisting of the following heterocyclic groups:

pyrrolyl; pyrazolyl; isoxazolyl; furanyl; thienyl; imidazolyl; oxazolyl; thiazolyl; isothiazolyl; triazolyl; oxadiazolyl; thiadiazolyl; tetrazolyl; furyl; pyridyl; pyrimidyl; pyrazinyl; pyridazinyl; triazinyl; pyranyl; quinazolinyl; isoquinolinyl; indolizinyl; isobenzofuranylnaphthyridinyl; quinoxalinyl; cinnolinyl; phthalazinyl; benzothiazolyl; benzoxazolyl; benzotriazolyl; indazolyl; indolyl; (1H-pyrrol-1-yl)-; (1H-pyrrol-2-yl)-; (1H-pyrrol-3-yl)-; (1H-pyrazol-1-yl)-; (1H-pyrazol-3-yl)-; (3H-pyrazol-3-yl)-; (1H-pyrazol-4-yl)-; (3-isoxazolyl)-; (5-isoxazolyl)-; (2-furanyl)-; (3-furanyl)-; (2-thienyl)-; (3-thienyl)-; (1H-imidazol-2-yl)-; (1H-imidazol-4-yl)-; (1H-imidazol-5-yl)-; (2-oxazol-2-yl)-; (oxazol-4-yl)-; (oxazol-5-yl)-; (thiazol-2-yl)-; (thiazol-4-yl)-; (thiazol-5-yl)-; (isothiazol-3-yl)-; (isothiazol-5-yl)-; (1H-1,2,3-triazol-1-yl)-; (1H-1,2,4-triazol-3-yl)-; (4H-1,2,4-triazol-4-yl)-; (1H-1,2,4-triazol-1-yl)-(1,2,3-oxadiazol-2-yl)-; (1,2,4-oxadiazol-3-yl)-; (1,2,4-oxadiazol-4-yl)-; (1,2,4-oxadiazol-5-yl)-; (1,2,3-thiadiazol-2-yl)-; (1,2,4-thiadiazol-3-yl)-; (1,2,4-thiadiazol-4-yl)-; (1,3,4-thiadiazol-5-yl)-; (1H-tetrazol-1-yl)-; (1H-tetrazol-5-yl)-; (2H-tetrazol-5-yl)-; (2-pyridyl)-; (3-pyridyl)-; (4-pyridyl)-; (2-pyrimidinyl)-;

(4-pyrimidinyl)-; (5-pyrimidinyl)-; (2-pyrazinyl)-; (3-pyridazinyl)-; (4-pyridazinyl)-; (1,3,5-triazin-2-yl)-; (1,2,4-triazin-5-yl)-; (1,2,4-triazin-6-yl)-; (1,2,4-triazin-3-yl)-; (furazan-3-yl)-; (2-quinolinyl)-; (3-quinolinyl)-; (4-quinolinyl)-; (5-quinolinyl)-; (6-quinolinyl)-; (3-isoquinolinyl)-; (4-isoquinolnyl)-; (2-quinozolinyl)-; (2-quinoxalinyl)-; (5-quinoxalinyl)-; (pyrido[2,3-b]pyrazin-7-yl)-; (benzoxazol-5-yl)-; (benzothiazol-5-yl)-; (benzo[b]thien-2-yl)- and (benzo[1,2,5]oxadiazol-5-yl)-; indolinyl and tetrahydroquinolynyl.

In preferred compounds of formula I, $R_3$ and $R_4$, independently from each other, are hydrogen, $C_1$-$C_4$ haloalkyl, halogen or selected from a group consisting of Z-0 to Z-50:

Z-0
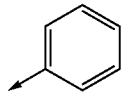

Z-1
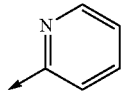

Z-2
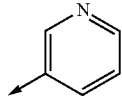

Z-3
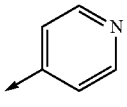

Z-4
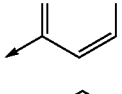

Z-5
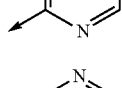

Z-6
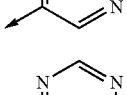

Z-7
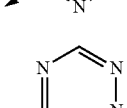

Z-8
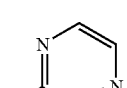

Z-9
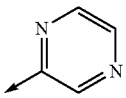

-continued

Z-10
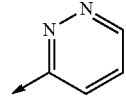

Z-11
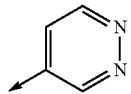

Z-12
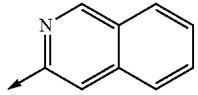

Z-13
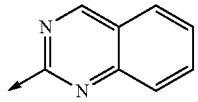

Z-14
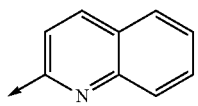

Z-15
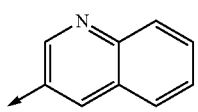

Z-16
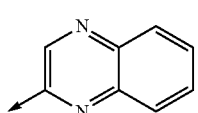

Z-17
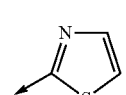

Z-18
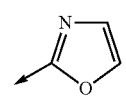

Z-19
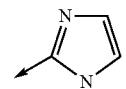

Z-20
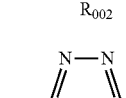

Z-21
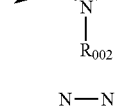

Z-22
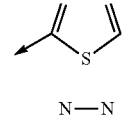

Z-23

Z-24
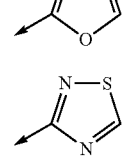

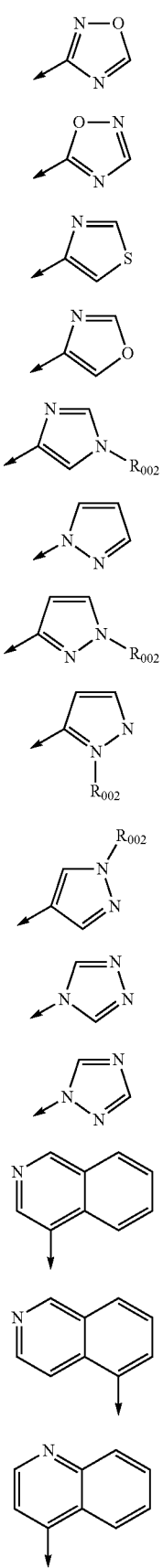
Z-25
Z-26
Z-27
Z-28
Z-29
Z-30
Z-31
Z-32
Z-33
Z-34
Z-35
Z-36
Z-37
Z-38
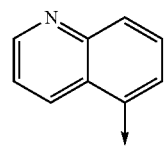
Z-39
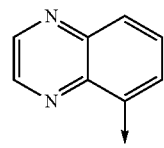
Z-40
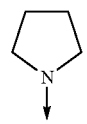
Z-41
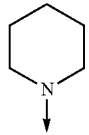
Z-42
Z-43
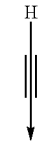
Z-44
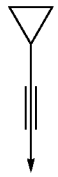
Z-45
Z-46
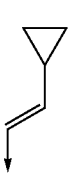
Z-47
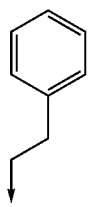
Z-48

-continued

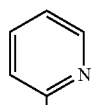
Z-49

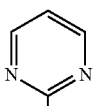
Z-50 wherein each group Z-0 to Z-50 is mono- di- or trisubstituted with Rx; wherein each Rx is, independently selected from the group consisting of hydrogen, halogen, cyano, $C_1$-$C_4$ alkyl, $C_1$-$C_4$ haloalkyl, $C_1$-$C_4$ haloalkoxy, $C_1$-$C_4$ alkoxy, $C_1$-$C_4$ alkylsulfanyl, $C_1$-$C_4$ alkylsulfinyl, $C_1$-$C_4$ alkylsulfonyl, —C(O)$C_1$-$C_4$ alkyl, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl; and $R_{002}$ represents hydrogen or $C_1$-$C_4$ haloalkyl.

The following embodiments of the invention are preferred:

EMBODIMENT A1

A preferred group of compounds of formula I is represented by the compounds of formula I-1

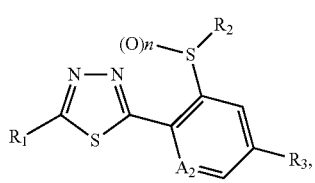
(I-1)

wherein $A_2$, $R_1$, $R_2$, n, and $R_3$ are as defined under formula I above.

More preferred compounds of formula I-1 are those, in which $A_2$ is methine or N; n is 0 or 2; $R_2$ is ethyl, cyclopropyl or cyclopropylmethyl; $R_1$ is selected from J-0, J-1, J-2, J-3, J-4, J-5, J-6, J-10, J-11, J-12, J-29 and J-30 wherein each of the groups J-0, J-1, J-2, J-3, J-4, J-5, J-6, J-10, J-11, J-12, J-29, J-30 can be mono, di- or tri-substiuted by a group Rx; wherein Rx is independently selected from the group consisting of hydrogen, halogen, cyano, $C_1$-$C_4$ alkyl, $C_1$-$C_4$ haloalkyl, $C_1$-$C_4$ haloalkoxy, $C_1$-$C_4$ alkoxy, $C_1$-$C_4$ alkylsulfanyl, $C_1$-$C_4$ alkylsulfinyl, $C_1$-$C_4$ alkylsulfonyl, —C(O)$C_1$-$C_4$ alkyl, —C(O)$C_1$-$C_4$ haloalkyl, $C_1$-$C_4$ haloalkylsulfanyl, $C_1$-$C_4$ haloalkylsulfinyl, and $C_1$-$C_4$ haloalkylsulfonyl;

and $R_3$ is hydrogen, $C_1$-$C_4$ haloalkyl, halogen or selected from a group consisting of Z-0, Z-1, Z-2, Z-3, Z-4, Z-5, Z-6, Z-10, Z11, Z-30, Z-35 and Z-43 wherein each group Z-0, Z-1, Z-2, Z-3, Z-4, Z-5, Z-6, Z-10, Z11, Z-30, Z-35 and Z-43 can be mono- di- or trisubstituted with Rx; wherein each Rx is, independently selected from the group consisting of hydrogen, halogen, cyano, $C_1$-$C_4$ alkyl, $C_1$-$C_4$ haloalkyl, $C_1$-$C_4$ haloalkoxy, $C_1$-$C_4$ alkoxy, $C_1$-$C_4$ alkylsulfanyl, $C_1$-$C_4$ alkylsulfinyl, $C_1$-$C_4$ alkylsulfonyl, —C(O)$C_1$-$C_4$ alkyl, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl.

More highly preferred compounds of formula I-1 are those, in which $A_2$ is methine or N; $R_2$ is ethyl; n is 2; $R_1$ is selected from the group consisting of J-1 and J-2 wherein each of the groups J-1, and J-2 can be mono- or di-substiuted by a group Rx; wherein Rx is independently selected from the group consisting of hydrogen, halogen, cyano, $C_1$-$C_4$ alkyl, and $C_1$-$C_4$ haloalkyl;

$R_3$ is hydrogen, $C_1$-$C_4$ haloalkyl or selected from a group consisting of Z-0, Z-1, Z-5, Z-30, and Z-43 wherein each group Z-0, Z-1, Z-5, Z-30, and Z-43 can be mono-substiututed with Rx; wherein each Rx is, independently selected from the group consisting of hydrogen, halogen, cyano, $C_1$-$C_4$ alkyl, and $C_1$-$C_4$ haloalkyl.

An even more highly preferred group of compounds of formula I-1 are those, in which which $A_2$ is methine or N; $R_2$ is ethyl; n is 2; $R_1$ is selected from the group consisting of J-1a, J-1b, J-1c and J-1d wherein Rx is $C_1$-$C_4$ haloalkyl; and $R_3$ is hydrogen, $C_1$-$C_4$ haloalkyl, halogen or selected from a group consisting of Z-0a, Z-1a, Z-5a, Z-30a and Z-43a

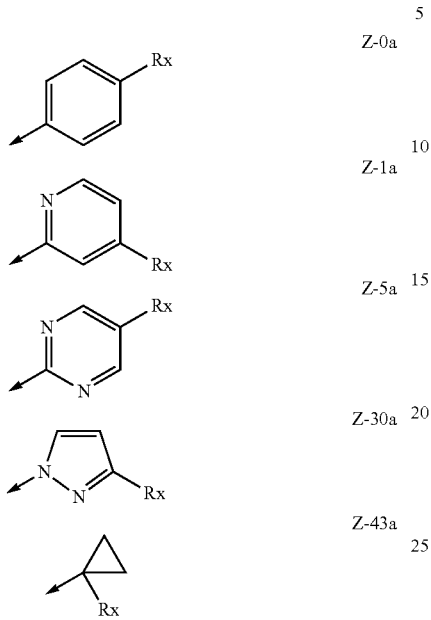

wherein each Rx is, independently selected from the group consisting of hydrogen, halogen, cyano, or $C_1$-$C_4$ haloalkyl.

In most highly preferred compounds of formula I-1, $A_2$ is N.

In a further preferred group of compounds of formula I-1, $A_2$ is methine.

In formula I-1 and all of the preferred embodiments of the formula I-1, $R_3$ is preferably hydrogen, $C_1$-$C_4$ haloalyl, $C_1$-$C_6$ cycloalkyl or pyrimidinyl.

EMBODIMENT A2

A preferred group of compounds of formula I is represented by the compounds of formula I-2

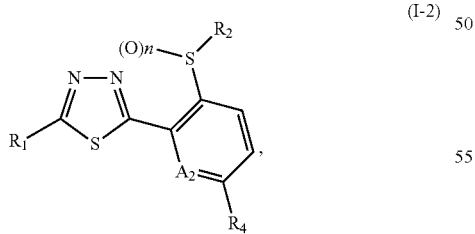

wherein $A_2$, $R_1$, $R_2$, n, and $R_4$ are as defined under formula I above.

More preferred compounds of formula I-2 are those, in which $A_2$ is methine or N; n is 0 or 2; $R_2$ is ethyl, cyclopropyl or cyclopropylmethyl; $R_1$ is selected from the group consisting of J-0, J-1, J-2, J-3, J-4, J-5, J-6, J-10, J-11, J-12, J-29 and J-30

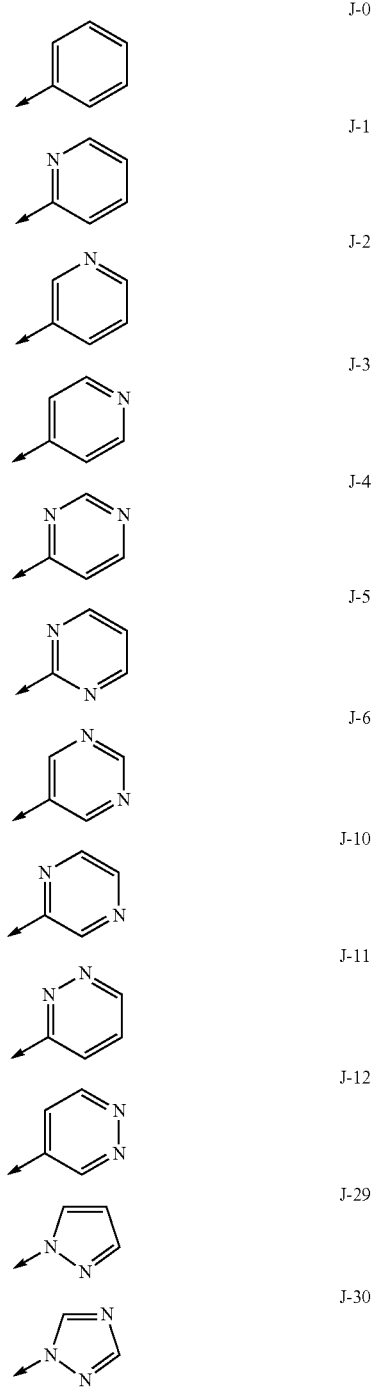

wherein each of the groups J-0, J-1, J-2, J-3, J-4, J-5, J-6, J-10, J-11, J-12, J-29, J-30 can be mono, di- or tri-substiuted by a group Rx, wherein Rx is independently selected from the group consisting of hydrogen, halogen, cyano, $C_1$-$C_4$ alkyl, $C_1$-$C_4$ haloalkyl, $C_1$-$C_4$ haloalkoxy, $C_1$-$C_4$ alkoxy, $C_1$-$C_4$ alkylsulfanyl, $C_1$-$C_4$ alkylsulfinyl, $C_1$-$C_4$ alkylsulfonyl, —C(O)$C_1$-$C_4$ alkyl, —C(O)$C_1$-$C_4$ haloalkyl, $C_1$-$C_4$ haloalkylsulfanyl, $C_1$-$C_4$ haloalkylsulfinyl, and $C_1$-$C_4$ haloalkylsulfonyl;

and $R_4$ is hydrogen, $C_1$-$C_4$ haloalkyl, halogen or selected from a group consisting of Z-0, Z-1, Z-2, Z-3, Z-4, Z-5, Z-6, Z-10, Z-11, Z-30, Z-35, and Z-43

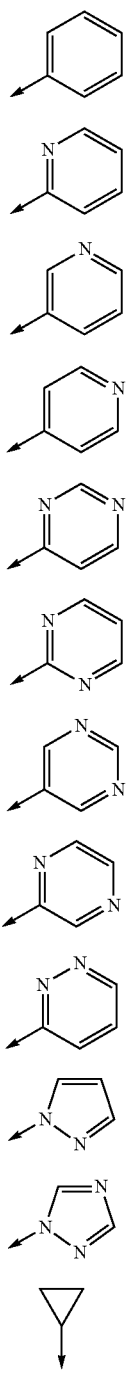

wherein each group Z-0, Z-1, Z-2, Z-3, Z-4, Z-5, Z-6, Z-10, Z11, Z-30, Z-35, and Z-43 can be mono- di- or trisubstituted with Rx; wherein each Rx is, independently selected from the group consisting of hydrogen, halogen, cyano, $C_1$-$C_4$ alkyl, $C_1$-$C_4$ haloalkyl, $C_1$-$C_4$ haloalkoxy, $C_1$-$C_4$ alkoxy, $C_1$-$C_4$ alkylsulfanyl, $C_1$-$C_4$ alkylsulfinyl, $C_1$-$C_4$ alkylsulfonyl, —C(O)$C_1$-$C_4$ alkyl, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl.

More highly prefered compounds of formula I-2 are those in which $A_2$ is methine or N; $R_2$ is ethyl; n is 2; $R_1$ is selected from the group consisting of J-1 and J-2

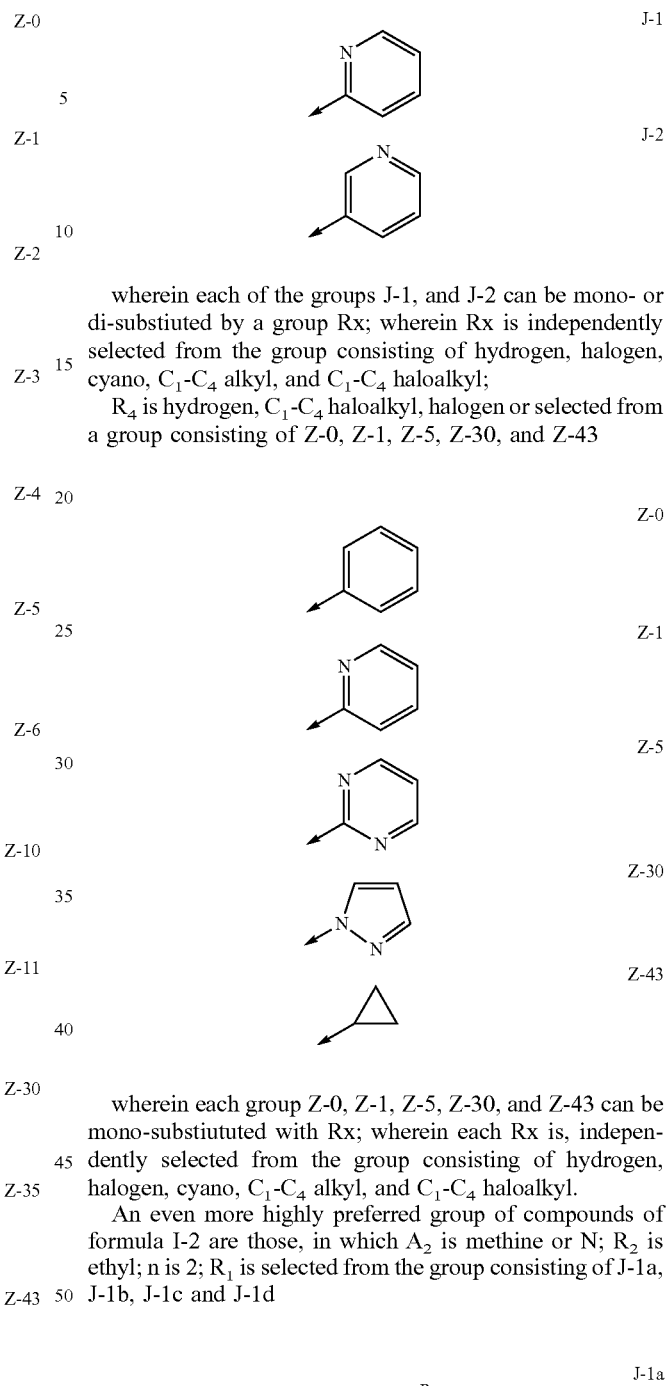

wherein each of the groups J-1, and J-2 can be mono- or di-substiuted by a group Rx; wherein Rx is independently selected from the group consisting of hydrogen, halogen, cyano, $C_1$-$C_4$ alkyl, and $C_1$-$C_4$ haloalkyl;

$R_4$ is hydrogen, $C_1$-$C_4$ haloalkyl, halogen or selected from a group consisting of Z-0, Z-1, Z-5, Z-30, and Z-43 wherein each group Z-0, Z-1, Z-5, Z-30, and Z-43 can be mono-substiututed with Rx; wherein each Rx is, independently selected from the group consisting of hydrogen, halogen, cyano, $C_1$-$C_4$ alkyl, and $C_1$-$C_4$ haloalkyl.

An even more highly preferred group of compounds of formula I-2 are those, in which $A_2$ is methine or N; $R_2$ is ethyl; n is 2; $R_1$ is selected from the group consisting of J-1a, J-1b, J-1c and J-1d

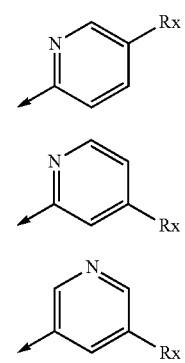

-continued

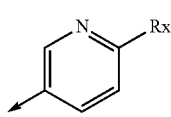
J-1d wherein Rx is $C_1$-$C_4$ haloalkyl; and $R_4$ is hydrogen, $C_1$-$C_4$ haloalkyl, halogen or selected from a group consisting of Z-0a, Z-1a, Z-5a, Z-30a and Z-43a

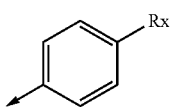
Z-0a

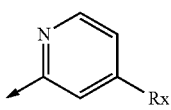
Z-1a

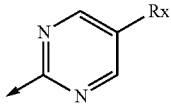
Z-5a

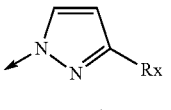
Z-30a

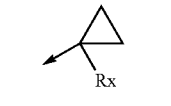
Z-43a wherein each Rx is, independently selected from the group consisting of hydrogen, halogen, cyano and $C_1$-$C_4$ haloalkyl.

In most highly preferred compounds of formula I-2, $A_2$ is N.

In a further preferred group of compounds of formula I-2, $A_2$ is methine.

In formula I-2 and all of the preferred embodiments of the formula I-2, $R_4$ is preferably hydrogen, $C_1$-$C_4$ haloalyl, $C_1$-$C_6$ cycloalkyl or pyrimidinyl.

EMBODIMENT A3

A preferred group of compounds of formula I is represented by the compounds of formula I-3

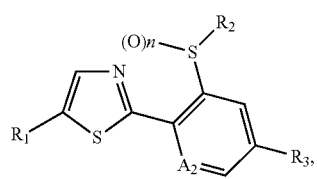
(I-3)

wherein $A_2$, $R_1$, $R_2$, n, and $R_3$ are as defined under formula I above.

More preferred compounds of formula I-3 are those, in which $A_2$ is methine or N; n is 0 or 2; $R_2$ is ethyl, cyclopropyl or cyclopropylmethyl, $R_1$ is selected from the group consisting of J-0, J-1, J-2, J-3, J-4, J-5, J-6, J-10, J-11, J-12, J-29 and J-30

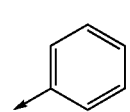
J-0

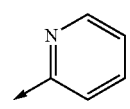
J-1

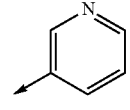
J-2

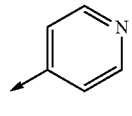
J-3

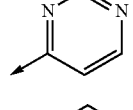
J-4

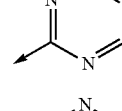
J-5

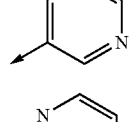
J-6

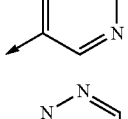
J-10

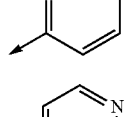
J-11

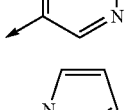
J-12

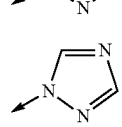
J-29

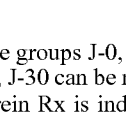
J-30 wherein each of the groups J-0, J-1, J-2, J-3, J-4, J-5, J-6, J-10, J-11, J-12, J-29, J-30 can be mono, di- or tri-substiuted by a group Rx; wherein Rx is independently selected from the group consisting of hydrogen, halogen, cyano, $C_1$-$C_4$ alkyl, $C_1$-$C_4$ haloalkyl, $C_1$-$C_4$ haloalkoxy, $C_1$-$C_4$ alkoxy, $C_1$-$C_4$ alkylsulfanyl, $C_1$-$C_4$ alkylsulfinyl, $C_1$-$C_4$ alkylsulfonyl, —C(O)$C_1$-$C_4$ alkyl, —C(O)$C_1$-$C_4$ haloalkyl, $C_1$-$C_4$ haloalkylsulfanyl, $C_1$-$C_4$ haloalkylsulfinyl, and $C_1$-$C_4$ haloalkylsulfonyl;

and $R_3$ is hydrogen, $C_1$-$C_4$ haloalkyl, halogen or selected from a group consisting of Z-0, Z-1, Z-2, Z-3, Z-4, Z-5, Z-6, Z-10, Z11, Z-30, Z-35 and Z-43

Z-0

Z-1

Z-2

Z-3

Z-4

Z-5

Z-6

Z-10

Z-11

Z-30

Z-35

Z-43 wherein each group Z-0, Z-1, Z-2, Z-3, Z-4, Z-5, Z-6, Z-10, Z11, Z-30, Z-35 and Z-43 can be mono- di- or trisubstituted with Rx; wherein each Rx is, independently selected from the group consisting of hydrogen, halogen, cyano, $C_1$-$C_4$ alkyl, $C_1$-$C_4$ haloalkyl, $C_1$-$C_4$ haloalkoxy, $C_1$-$C_4$ alkoxy, $C_1$-$C_4$ alkylsulfanyl, $C_1$-$C_4$ alkylsulfinyl, $C_1$-$C_4$ alkylsulfonyl, —C(O)$C_1$-$C_4$ alkyl, $C_1$-$C_4$ haloalkylsulfanyl, $C_1$-$C_4$ haloalkylsulfinyl, $C_1$-$C_4$ haloalkylsulfonyl and —C(O)$C_1$-$C_4$ haloalkyl.

More highly preferred compounds of formula I-3 are those, in which $A_2$ is methine or N; $R_2$ is ethyl; n is 2; $R_1$ is selected from the group consisting of J-1 and J-2

J-1

J-2 wherein each of the groups J-1 and J-2 can be mono- or di-substituted by a group Rx; wherein Rx is independently selected from the group consisting of hydrogen, halogen, cyano, $C_1$-$C_4$ alkyl, and $C_1$-$C_4$ haloalkyl;

$R_3$ is hydrogen, $C_1$-$C_4$ haloalkyl or selected from a group consisting of Z-0, Z-1, Z-5, Z-30 and Z-43

Z-0

Z-1

Z-5

Z-30

Z-43 wherein each group Z-0, Z-1, Z-5, Z-30 and Z-43 can be mono-substiututed with Rx, wherein each Rx is, independently selected from the group consisting of hydrogen, halogen, cyano, $C_1$-$C_4$ alkyl, and $C_1$-$C_4$ haloalkyl.

An even more highly preferred group of compounds of formula I-3 are those, in which $A_2$ is methine or N; $R_2$ is ethyl; n is 2; $R_1$ is selected from the group consisting of J-1a, J-1 b, J-1c and J-1d J-1a J-1b J-1c -continued

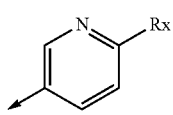
J-1d wherein Rx independently is $C_1$-$C_4$ haloalkyl;
and $R_3$ is hydrogen, $C_1$-$C_4$ haloalkyl, halogen or selected from a group consisting of Z-0a, Z-1a, Z-5a, Z-30a and Z-43a

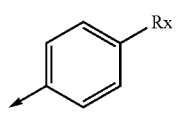
Z-0a

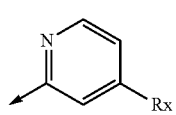
Z-1a

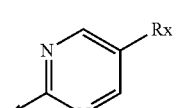
Z-5a

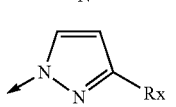
Z-30a

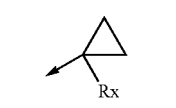
Z-43a wherein each Rx is, independently selected from the group consisting of hydrogen, halogen, cyano and $C_1$-$C_4$ haloalkyl.

In most highly preferred compounds of formula I-3, $A_2$ is N.

In a further preferred group of compounds of formula I-3, $A_2$ is methine.

In formula I-3 and all of the preferred embodiments of the formula I-3, $R_3$ is preferably hydrogen, $C_1$-$C_4$ haloalyl, $C_1$-$C_6$ cycloalkyl or pyrimidinyl.

EMBODIMENT A4

A preferred group of compounds of formula I is represented by the compounds of formula I-4

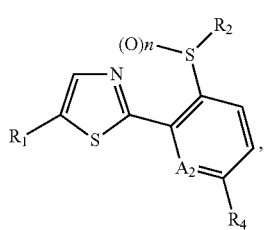
(I-4)

wherein $A_2$, $R_1$, $R_2$, n, and $R_4$ are as defined under formula I above.

More preferred compounds of formula I-4 are those, in which $A_2$ is methine or N; n is 0 or 2; $R_2$ is ethyl, cyclopropyl or cyclopropylmethyl; $R_1$ is selected from the group consisting of J-0, J-1, J-2, J-3, J-4, J-5, J-6, J-10, J-11, J-12, J-29 and J-30

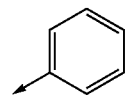
J-0

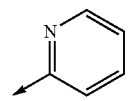
J-1

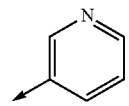
J-2

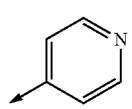
J-3

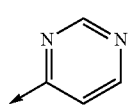
J-4

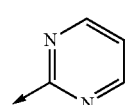
J-5

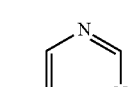
J-6

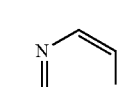
J-10

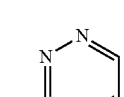
J-11

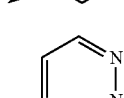
J-12

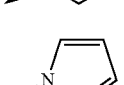
J-29

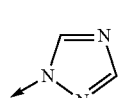
J-30 wherein each of the groups J-0, J-1, J-2, J-3, J-4, J-5, J-6, J-10, J-11, J-12, J-29 and J-30 can be mono, di- or tri-substiuted by a group Rx; wherein Rx is independently selected from the group consisting of hydrogen, halogen, cyano, $C_1$-$C_4$ alkyl, $C_1$-$C_4$ haloalkyl, $C_1$-$C_4$ haloalkoxy, $C_1$-$C_4$ alkoxy, $C_1$-$C_4$ alkylsulfanyl, $C_1$-$C_4$ alkylsulfinyl, C₁-C₄ alkylsulfonyl, —C(O)C₁-C₄ alkyl, —C(O)C₁-C₄ haloalkyl, C₁-C₄ haloalkylsulfanyl, C₁-C₄ haloalkylsulfinyl, and C₁-C₄ haloalkylsulfonyl;

and R₄ is hydrogen, C₁-C₄ haloalkyl, halogen or selected from a group consisting of Z-0, Z-1, Z-2, Z-3, Z-4, Z-5, Z-6, Z-10, Z11, Z-30, Z-35 and Z-43;

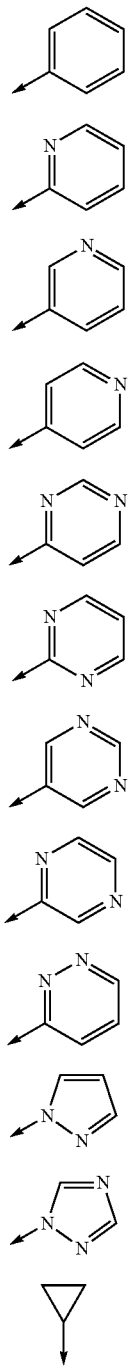

wherein each group Z-0, Z-1, Z-2, Z-3, Z-4, Z-5, Z-6, Z-10, Z11, Z-30, Z-35 and Z-43 can be mono- di- or trisubstituted with Rx; wherein each Rx is, independently selected from the group consisting of hydrogen, halogen, cyano, C₁-C₄ alkyl, C₁-C₄ haloalkyl, C₁-C₄ haloalkoxy, C₁-C₄ alkoxy, C₁-C₄ alkylsulfanyl, C₁-C₄ alkylsulfinyl, C₁-C₄ alkylsulfonyl, —C(O)C₁-C₄ alkyl, C₁-C₄ haloalkylsulfanyl, C₁-C₄ haloalkylsulfinyl, C₁-C₄ haloalkylsulfonyl and —C(O)C₁-C₄ haloalkyl;

More highly preferred compounds of formula I-4 are those, in which A₂ is methine or N; R₂ is ethyl; n is 2; R₁ is selected from the group consisting of J-1 and J-2

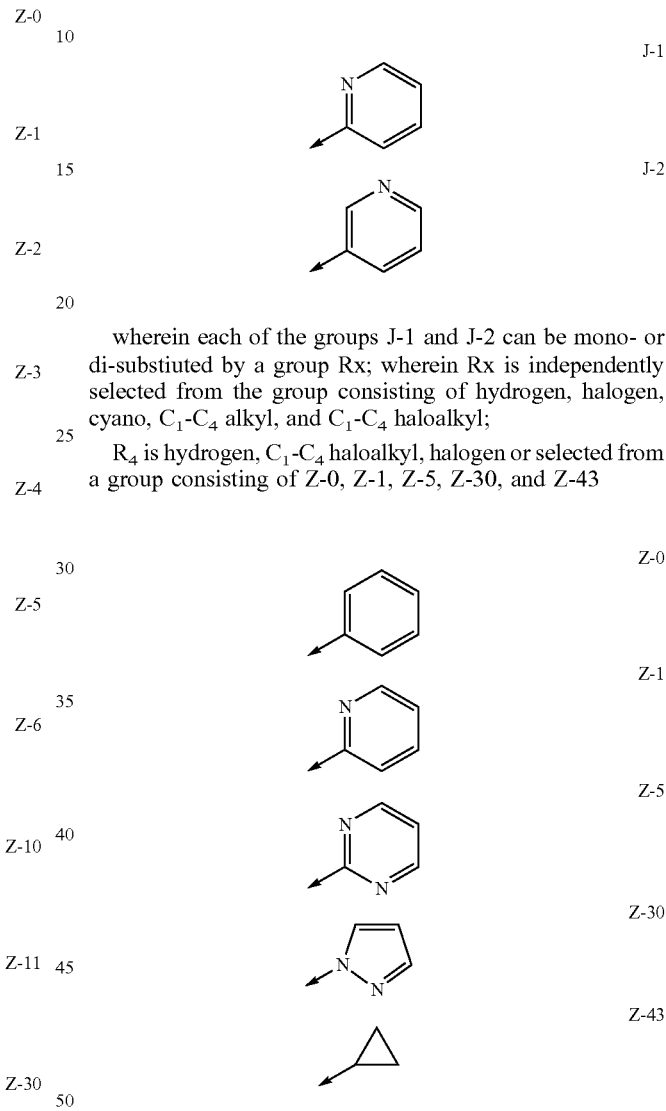

wherein each of the groups J-1 and J-2 can be mono- or di-substiututed by a group Rx; wherein Rx is independently selected from the group consisting of hydrogen, halogen, cyano, C₁-C₄ alkyl, and C₁-C₄ haloalkyl;

R₄ is hydrogen, C₁-C₄ haloalkyl, halogen or selected from a group consisting of Z-0, Z-1, Z-5, Z-30, and Z-43 wherein each group Z-0, Z-1, Z-5, Z-30 and Z-43 can be mono-substiututed with Rx; wherein each Rx is, independently selected from the group consisting of hydrogen, halogen, cyano, C₁-C₄ alkyl and C₁-C₄ haloalkyl.

An even more highly preferred group of compounds of formula I-4 are those, in which A₂ is methine or N;

R₂ is ethyl; n is 2; R₁ is selected from the group consisting of J-1a, J-1b, J-1c and J-1d

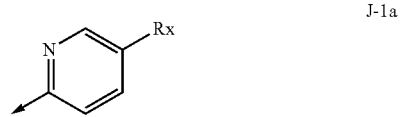

-continued

J-1b

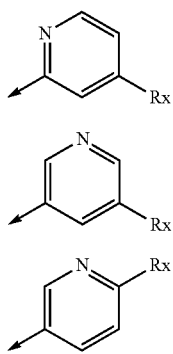

J-1c

J-1d wherein Rx independently is $C_1$-$C_4$ haloalkyl; and $R_4$ is hydrogen, $C_1$-$C_4$ haloalkyl, halogen or selected from a group group consisting of Z-0a, Z-1a, Z-5a, Z-30a and Z-43a

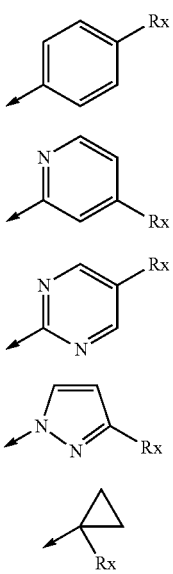

Z-0a

Z-1a

Z-5a

Z-30a

Z-43a wherein each Rx is, independently selected from the group consisting of hydrogen, halogen, cyano, or $C_1$-$C_4$ haloalkyl.

In most highly preferred compounds of formula I-4, $A_2$ is N.

In a further preferred group of compounds of formula I-4, $A_2$ is methine.

In formula I-4 and all of the preferred embodiments of the formula I-4, $R_4$ is preferably hydrogen, $C_1$-$C_4$ haloalyl, $C_1$-$C_6$ cycloalkyl or pyrimidinyl.

In an especially preferred embodiment A5, $R_1$ is pyridine which can monosubstituted by $C_1$-$C_4$ haloalkyl;

$R_2$ is $C_1$-$C_4$ alkyl;

$R_3$ is hydrogen, $C_1$-$C_4$ haloalyl, $C_1$-$C_6$ cycloalkyl or pyrimidinyl;

$R_4$ is hydrogen, $C_1$-$C_4$ haloalyl, $C_1$-$C_6$ cycloalkyl or pyrimidinyl;

n is 2;

$A_1$ is methine or N; and $A_2$ is methine or N.

The process according to the invention for preparing compounds of formula I is carried out by methods known to those skilled in the art, and as described below:

Compounds of formula I, respectively Ia,

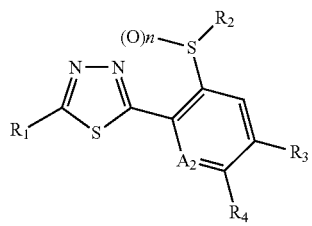

(Ia)

wherein $A_1$ is nitrogen; and $A_2$, $R_1$, $R_2$, $R_3$ and $R_4$ are as defined in formula I, can be prepared by reaction of a compound of formula II,

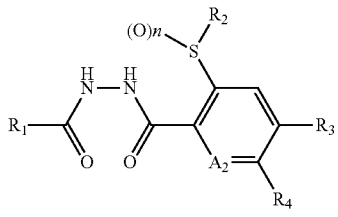

(II)

with a thionation reagent, for example Lawesson's reagent or phosphorus(V)sulfide, in an inert solvent such tetrahydrofurane, dioxane, toluene, dioxane, or xylenes at temperatures between 30-130° C. optionally in a microwave. Such reactions are well known in the literature and described for example in *Organic Preparations and Procedures International*, 37(3), 213-222, 2005 and *Journal fuer Praktische Chemie*, 322(6), 933-44, 1980. Compounds of formula Ia obtained, where n is 0 (the sulphide) can then be oxidized to compounds of formula I where n is 1 (sulphoxide) or n is 2 (suphone) by methods known to those skilled in the art. More specifically, the subgroup of compounds of formula Ia, wherein n is 1 (sulfoxide) and/or n is 2 (sulfone), may be obtained by means of an oxidation involving reagents such as, for example, m-chloroperoxybenzoic acid (mCPBA), hydrogen peroxide, oxone, sodium periodate, sodium hypochlorite or tert-butyl hypochlorite amongst other oxidants. The oxidation reaction is generally conducted in the presence of a solvent. Examples of the solvent to be used in the reaction include aliphatic halogenated hydrocarbons such as dichloromethane and chloroform; alcohols such as methanol and ethanol; acetic acid; water; and mixtures thereof. The amount of the oxidant to be used in the reaction is generally 1 to 3 moles, preferably 1 to 1.2 moles, relative to 1 mole of the sulfide compounds I to produce the sulfoxide compounds I, and preferably 2 to 2.2 moles of oxidant, relative to 1 mole of of the sulfide compounds I to produce the sulfone compounds I. Such oxidation reactions are disclosed, for example, in WO 2013/018928. The chemistry is summarized in scheme 1.

Scheme 1.

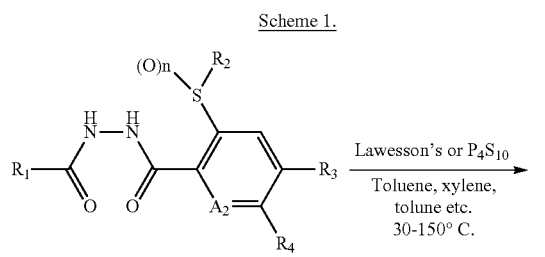

II, n is 0

Lawesson's or P$_4$S$_{10}$
Toluene, xylene, tolune etc.
30-150° C.

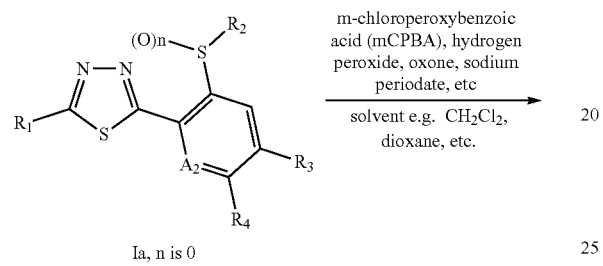

Ia, n is 0 m-chloroperoxybenzoic acid (mCPBA), hydrogen peroxide, oxone, sodium periodate, etc
solvent e.g. CH$_2$Cl$_2$, dioxane, etc.

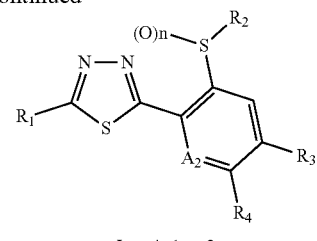

Ia, n is 1 or 2

Lawesson's or P$_4$S$_{10}$
Toluene, xylene, tolune etc.
30-150° C.

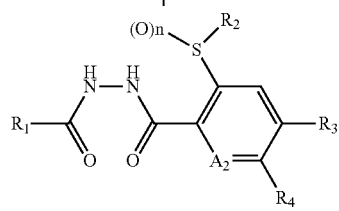

II, n is 1 or 2

Compounds of formula II may be prepared as shown in scheme 2.

Scheme 2

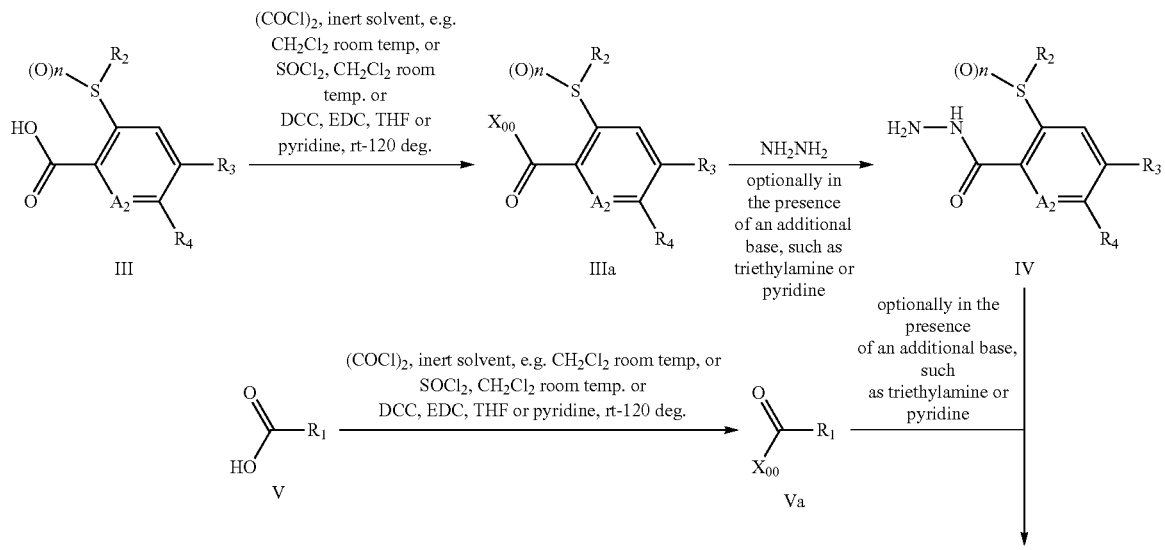

III (COCl)$_2$, inert solvent, e.g. CH$_2$Cl$_2$ room temp, or SOCl$_2$, CH$_2$Cl$_2$ room temp. or DCC, EDC, THF or pyridine, rt-120 deg.

IIIa

NH$_2$NH$_2$
optionally in the presence of an additional base, such as triethylamine or pyridine

IV optionally in the presence of an additional base, such as triethylamine or pyridine

V (COCl)$_2$, inert solvent, e.g. CH$_2$Cl$_2$ room temp, or SOCl$_2$, CH$_2$Cl$_2$ room temp. or DCC, EDC, THF or pyridine, rt-120 deg.

Va

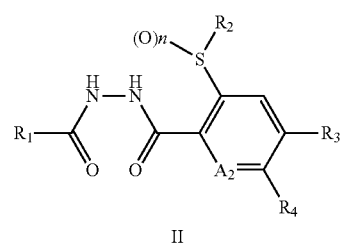

II

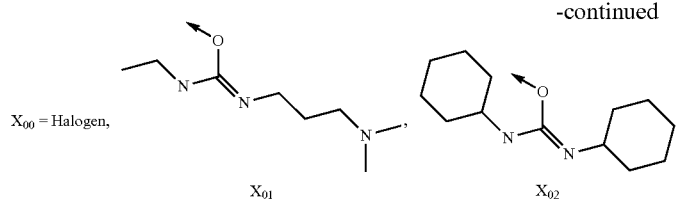

$X_{00}$ = Halogen,

This involves:

i) activation of compound of formula III, wherein n, $R_2$, $R_3$, $R_4$, $A_2$ are as defined above, by methods known to those skilled in the art and described in, for example, *Tetrahedron*, 2005, 61 (46), 10827-10852, to form an activated species IIIa, wherein n, $R_2$, $R_3$, $R_4$, $A_2$ is as defined above and wherein $X_{00}$ is halogen, preferably chlorine. For example, compounds IIIa where $X_{00}$ is halogen, preferably chlorine, are formed by treatment of III with, for example, oxallyl chloride $(COCl)_2$ or thionyl chloride $SOCl_2$ in the presence of catalytic quantities of N,N-dimethylformamide DMF in inert solvents such as methylene chloride $CH_2Cl_2$ or tetrahydrofurane THF at temperatures between 20 to 100° C., preferably 25° C.

Alternatively, treatment of compounds of formula III with, for example, 1-ethyl-3-(3-dimethylaminopropyl)carbodiimide EDC or dicyclohexyl carbodiimide DCC will generate an activated species IIIa, wherein $X_{00}$ is $X_{01}$ or $X_{02}$ respectively, in an inert solvent, such as pyridine or tetrahydrofuran THF, optionally in the presence of a base, such as triethylamine, at temperatures between 50-180° C.; followed by ii) Treatment of the activated species IIIa with hydrazine $NH_2NH_2$ (or a salt thereof), possibly in form of a hydrate, preferably hydrazine monohydrate, optionally in the presence of a base, such as triethylamine or pyridine, in an inert solvents such as dichloromethane, tetrahydrofuran, dioxane or toluene, at temperatures between 0 and 50° C., to form the compounds of formula IV.

Alternatively, compounds of the formula IV, or a salt thereof, wherein n, $R_2$, $R_3$, $R_4$, $A_2$ are as defined above, may be prepared by the direct action of hydrazine (or a salt thereof), possibly in form of a hydrate, preferably hydrazine monohydrate, on an ester derivative IIIb

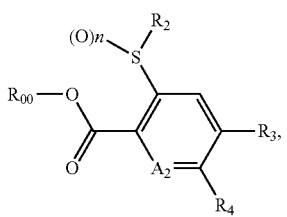

(IIIb)

of the compound of formula III, wherein n, $R_2$, $R_3$, $R_4$, $A_2$ are as described in formula I, and wherein $R_{00}$ is $C_1$-$C_4$ alkyl, preferably methyl or ethyl, at temperatures between 20 and 150° C. Such a process description may be found, for example, in M. H. Klingele et al, *Eur. J. Org. Chem.* 2004, 3422-3434. The compounds of formula IV obtained can be reacted with a compound of formula Va, wherein $R_1$ is as described as in formula I and $X_{00}$ is halogen, $X_{01}$ or $X_{02}$ (where $X_{01}$ and $X_{02}$ are as previously described) in an inert solvent such as toluene, tetrahydrofurane, methylene chloride, optionaly in the presence of a base, such as triethylamine. Compounds of formula Va are prepared from compounds of formula V, wherein $R_1$ is as described in formula I, by the same conditions used to prepare IIIa. Many similar reactions are known in the literature, see for example *Organic Letters*, 2015, 17(3), 438-441, *Organic & Biomolecular Chemistry*, 2013, 11(5), 732-745, and *J. Am. Chem. Soc.*, 2004 126(39), 12386-12394.

Compounds of formula V are known or can be prepared as described in the literature. Compounds of formula III are in many cases known in the literature (for example in WO 2015000715).

One synthesis of compounds of formula III, wherein $R_4$ is hydrogen, and $R_3$ is the group Z-0 to Z-50, as shown in scheme 3, begins with a Suzuki reaction, which involves for example, reacting compounds of formula VI, wherein $Xb_2$ is a leaving group like, for example, chlorine, bromine or iodine, or an aryl- or alkylsulfonate such as trifluoromethanesulfonate and $Xb_1$ is a leaving group, for example nitro, fluoro, bromo, chloro, $R_{00}$ is $C_1$-$C_4$ alkyl and $A_2$ is as described in formula I, with compounds of formula VII, wherein $Y_{b1}$ can be a boron-derived functional group, as for example $B(OH)_2$ or $B(OR_{b1})_2$ wherein $R_{b1}$ can be a $C_1$-$C_4$ alkyl group or the two groups $OR_{b1}$ can form together with the boron atom a five membered ring, as for example a pinacol boronic ester. The reaction can be catalyzed by a palladium based catalyst, for example tetrakis(triphenylphosphine)-palladium or (1,1'bis(diphenylphosphino)-ferrocene)dichloropalladium-dichloromethane (1:1 complex), in presence of a base, like sodium carbonate or cesium fluoride, in a solvent or a solvent mixture, like, for example a mixture of 1,2-dimethoxyethane and water or of dioxane and water, preferably under inert atmosphere, to give compounds of formula VIII. The reaction temperature can preferentially range from room temperature to the boiling point of the reaction mixture. Such Suzuki reactions are well known to those skilled in the art and have been reviewed, for example *J. Orgmet. Chem.* 576, 1999, 147-168.

Alternatively compounds of formula VIII can be prepared by a Stille reaction of compounds of formula VIIa wherein $Y_{b2}$ is a trialkyl tin derivative, preferably tri-n-butyl tin, with compounds of formula VI. Such Stille reactions are usually carried out in the presence of a palladium catalyst, for example tetrakis(triphenylphosphine)palladium(0), or (1,1'bis(diphenylphosphino)-ferrocene)dichloropalladium-dichloromethane (1:1 complex), in an inert solvent such as DMF, acetonitrile, or dioxane, optionally in the presence of an additive, such as cesium fluoride, or lithium chloride, and optionally in the presence of a further catalyst, for example copper(I)iodide. Such Stille couplings are also well known to those skilled in the art, and have been described in for example *J. Org. Chem.*, 2005, 70, 8601-8604, *J. Org. Chem.*, 2009, 74, 5599-5602, and *Angew. Chem. Int. Ed.*, 2004, 43, 1132-1136.

reagents such as, for example a peracid as peracetic acid or m-chloroperbenzoic acid, or a hydroperoxide as for example hydrogen peroxide or tert-butylhydroperoxide, or an inorganic oxidant, like a mono-peroxodisulfate salt or potassium permanganate, preferentially meta-chloroperbenzoic acid.

Those skilled in the art will realise that the compounds of formula III can be prepared in an alternative manner by switching the order of the previously described reactions. This is illustrated in scheme 4.

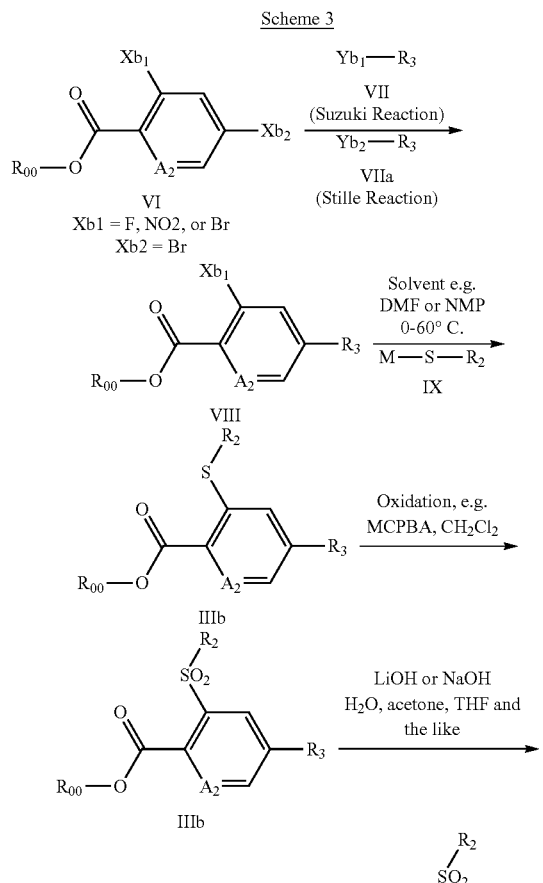

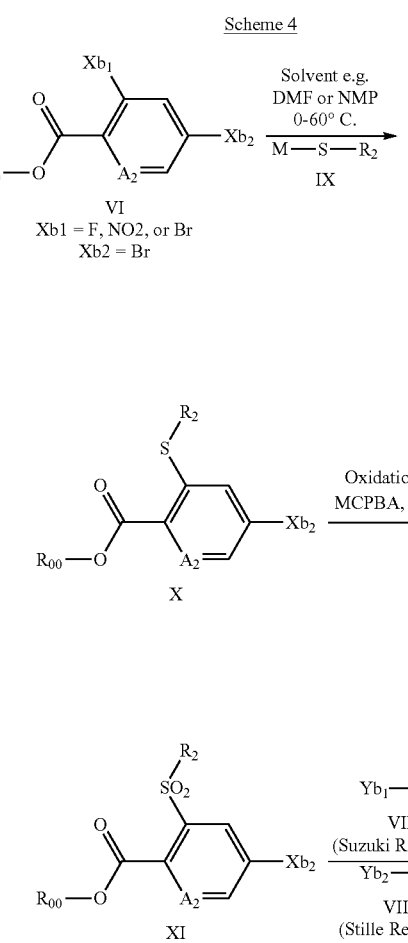

The compounds of formula VIII, wherein $A_2$, and $R_3$ are as described in formula I, and $R_{00}$ is $C_1$-$C_4$ alkyl are then reacted with a compound of the formula IX, wherein $R_2$ is as defined in formula I, and M is a metal or non-metal cation, to give compounds of formula III, respectively IIIa wherein $R_2$, $R_3$, and $R_{00}$ are as previously described. In scheme 3, the cation M is assumed to be monovalent, but polyvalent cations associated with more than one S—$R_2$ group can also be considered. Preferred cations are, for example lithium, sodium, potassium or caesium. The reaction can be performed in a solvent, preferably polar aprotic, at temperatures below 0° C. or up to boiling temperature of the reaction mixture. Such reactions are well known and described for example in WO 2015/000715. Oxidation of compounds III to compounds of formula IIIb can be performed with

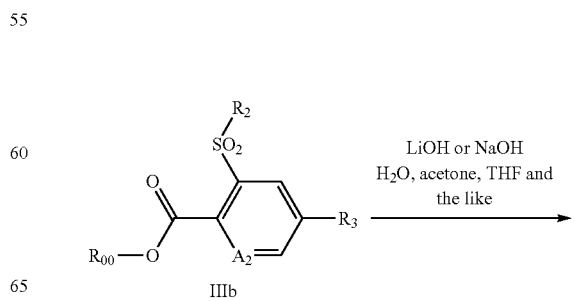

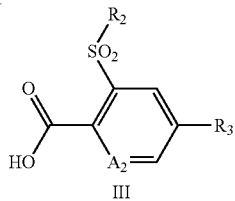

A large number of compounds of the formula VI are commercially available or can be prepared by those skilled in the art. Many chemical transformations, well known by those skilled in the art, can be used to access boronic acid derivatives of formula VII, starting from various and easily available starting materials, as for example, to cite only a few (scheme 5), hydrogen abstraction on a heteroaromatic compound of the formula $VII_1$ wherein $Zb_1$ is hydrogen, with a strong base (step A), like butyl lithium or lithium diisopropylamide or (i-PrMgCl. LiCl), followed by reaction of the metallated intermediate of the formula $VII_2$, wherein $Zb_2$ is a metal such as $Li^+$ or $MgCl^+$ for example, with, for example, a trialkylborate (step B), or a tri-n-butyl tin chloride (step B). Another way to access an organometal intermediate of the formula $VII_2$ is from a compound of the formula $VII_1$ wherein $Zb_1$ is chlorine, bromine or iodine, via metal-halogen exchange with an organometallic species (step C), like butyl lithium or an organo magnesium compound, or direct metallation with a metal, like magnesium.

Introduction of a pinacolborate functional group via palladium catalyzed reaction with bispinacol diborane, or hexan-butyldistannane, on a compound of the formula $VII_1$, wherein $Zb_1$ is chlorine, bromine, iodine or triflate, is another common strategy (scheme 5, step D). In the compounds of formula VII, VIIa, $VII_2$, and $VII_2$ within scheme 5, $R_3$ has the values defined for the formula I. A person skilled in the art will be able to select an adequate preparation method to access compounds of formula VII, VIIa, $VII_2$, and $VII_2$ depending on the values of $R_3$.

Compounds of formula IIIc wherein $R_3$ is a nitrogen bearing hetereocyclic system, $R_{00}$ is as previously defined, and $A_2$ is as defined in formula I, can be prepared from compounds of formula XI, wherein Xb2 is as previously defined, by reacting the hetreocycle $R_3$ (which contains a an appropriate NH functionality), in the presence of a base, such as $K_2CO_3$ or $Cs_2CO_3$, optionally in the presence of a copper catalyst, for example copper (I) iodide in an inert solvent such as n-methyl pyrollidione or DMF at temperatures between 30-150° C. The reaction is illustrated for the heterocycle Z-30a in scheme 6, to give compounds of formula IIIc, wherein $R_2$, $R_{00}$, and $A_2$ are as previously defined.

Scheme 6

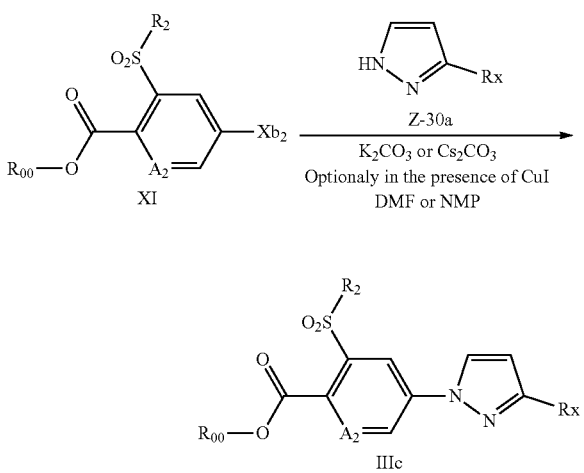

Compounds of formula III where $R_3$ is H, $A_2$ is N, and $R_4$ is a group Z-0 to Z-50 can be synthesized as shown in scheme 7.

Scheme 5

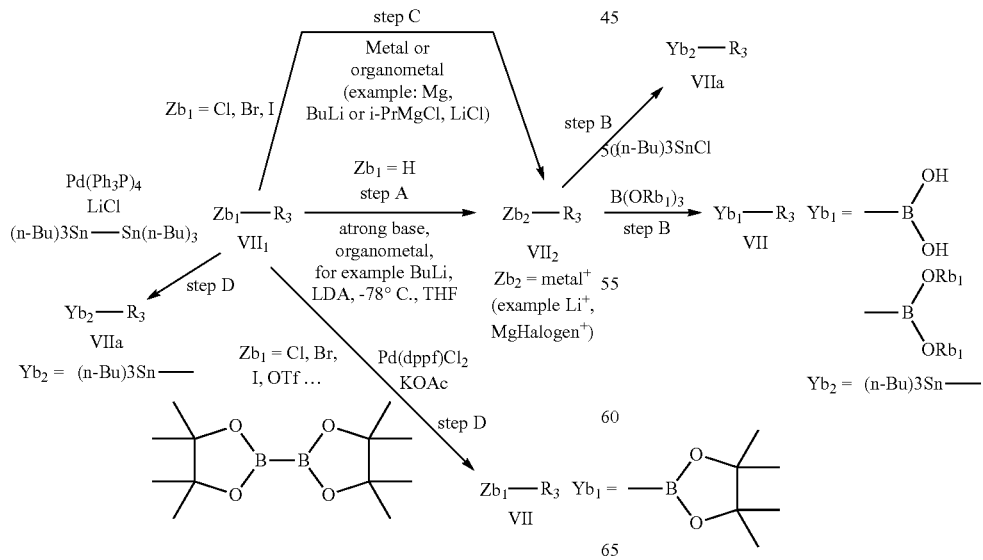

Scheme 7.

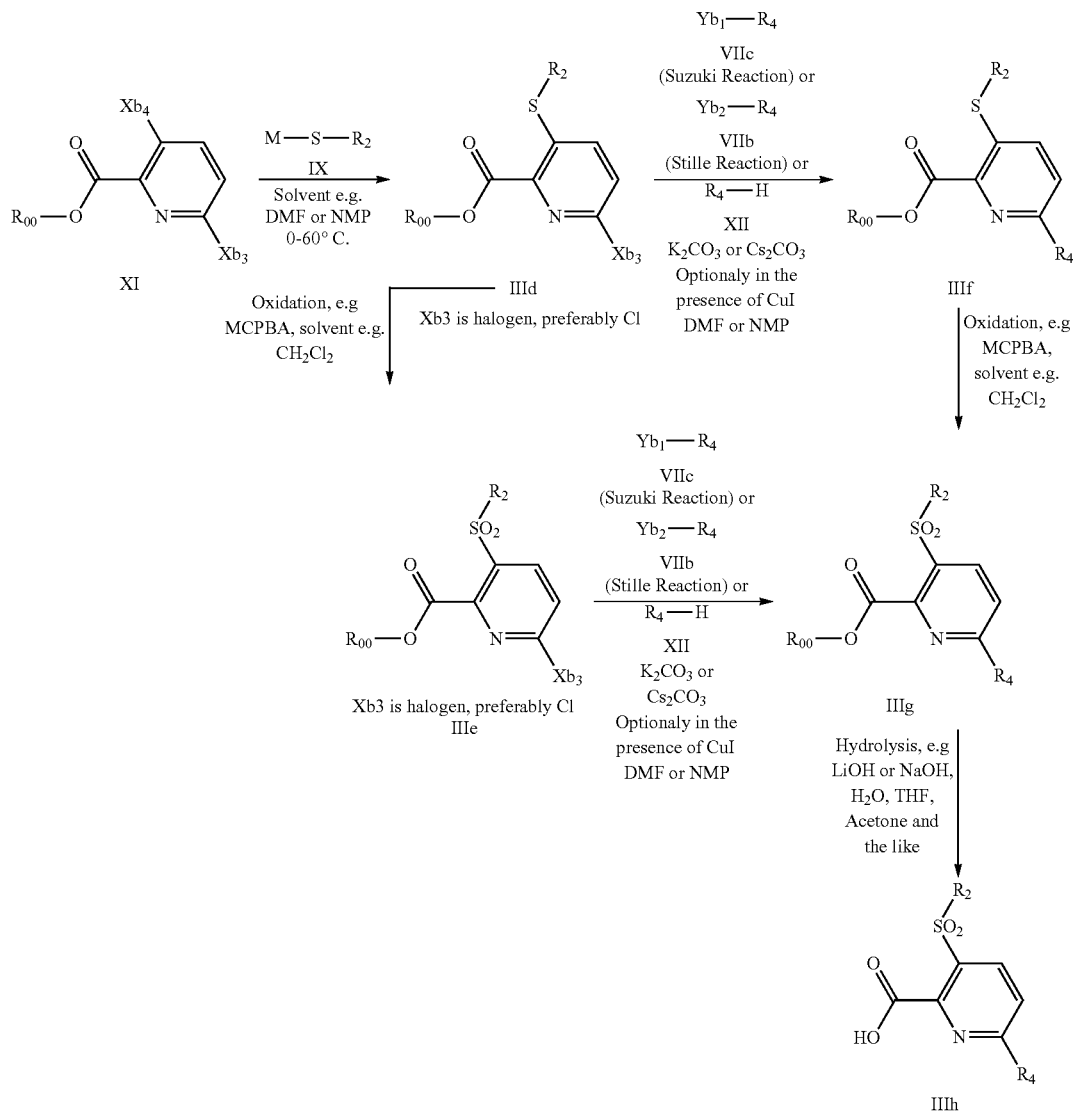

In scheme 7, a compound of formula XI wherein Xb4 and Xb3 are halogen, preferably chloro, and $R_{00}$ is $C_1$-$C_4$ alkyl is reacted with a compound of formula IX (as discussed for the preparation of IIIb in scheme 3) to give a compound IIId, wherein $R_2$ is as defined in formula I. Alternatively, compounds of formula IX can be reacted with compounds of formula XI in THF in the presence of the appropriate crown ether complex for the cation M. The compound IIId obtained can be reacted under Suzuki conditions with a compound VIIc, wherein $R_4$ is a group Z-0 to Z-50 and wherein is $Y_{b1}$ can be a boron-derived functional group, as for example $B(OH)_2$ or $B(OR_{b1})_2$ wherein $R_{b1}$ can be a $C_1$-$C_4$ alkyl group or the two groups $OR_{b1}$ can form together with the boron atom a five membered ring, as for example a pinacol boronic ester, to give compounds of formula IIIf. This type of Suzuki reaction was discussed previously in context for the preparation of compounds of formula VIII in scheme 3. Alternatively, compounds of formula VIIb, wherein $R_4$ is a group Z-0 to Z-50 and wherein $Y_{b2}$ is a trialkyl tin derivative, preferably tri-n-butyltin, can be reacted under Stille conditions as discussed for the preparation of compound VIII in scheme 3 with compounds of formula IIId to give compounds of formula IIIf. Oxidation of compounds IIIf to compounds of formula IIIg can be performed with reagents like, for example a peracid as peracetic acid or m-chloroperbenzoic acid, or a hydroperoxide as for example hydrogen peroxide or tert-butylhydroperoxide, or an inorganic oxidant, like a mono-peroxodisulfate salt or potassium permanganate, preferentially meta-chloroperbenzoic acid. Those skilled in the art will realise that the order of the reactions can be switched, and that it is possible to first oxidise compound IIId to compound IIIe and then carry out Stille or Suzuki reactions as previously discussed with compounds of formula VIIb and VIIc, respectively, to give compounds of formula IIIg. Compounds of formula IIIg wherein $R_4$ is a nitrogen bearing heterocyclic system, can also be prepared from compounds of formula IIIe, wherein Xb3 is halogen, by reacting compounds of formula XII (wherein $R_4$ is a group Z-30, Z-34, Z-35, Z-41 or Z-42 which contains a an appropriate NH functionality), in the presence of a base, such as K$_2$CO$_3$ or Cs$_2$CO$_3$, optionally in the presence of a copper catalyst, for example copper (I) iodide in an inert solvent such as n-methyl pyrollidione or DMF at temperatures between 30-150° C. Subsequent oxidation as previously described will deliver compounds of formula IIIg. Alternatively, compounds of formula IIIg can be prepared by reversing the order of the reactions (i.e oxidation of compound IIId to IIIe and then reaction with compounds of formula XII, VIIc, and VIIb to give the compounds IIIg). Compounds of formula IIIg can be hydrolyzed to the corresponding acids IIIh by methods known to those skilled in the art. Compounds of formula VIIb and VIIc can be prepared analogously to compound VII and VIIa, shown in scheme 5.

Compounds of formula I wherein R$_1$, R$_2$, A$_2$, R$_3$, R$_4$ and n are as described in formula I and A$_1$ is methine, namely compounds of formula Ib:

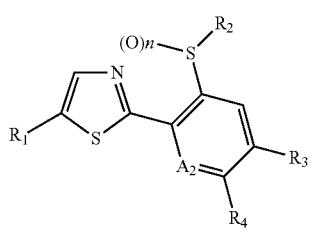
(Ib)

can be prepared as shown in scheme 8:

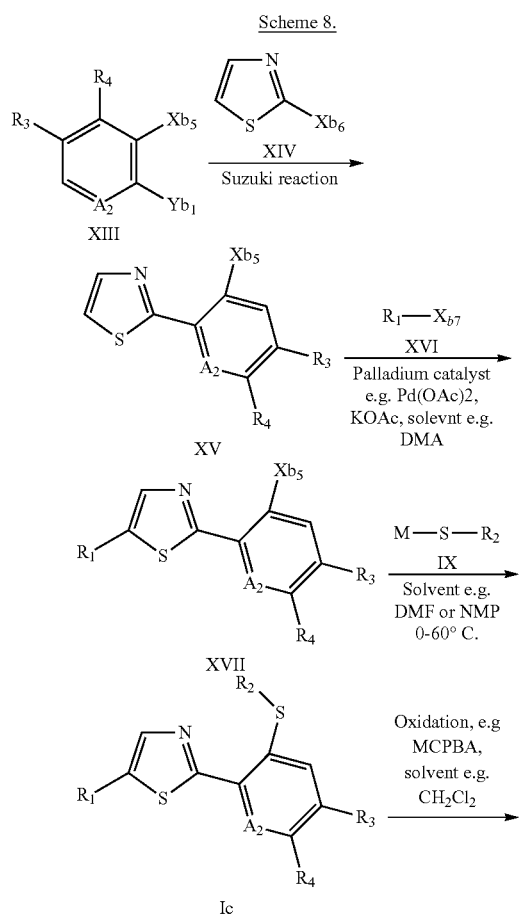

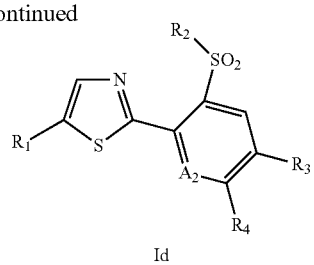
Id

As shown in scheme 8, compounds of formula XIII, wherein R$_3$, R$_4$ and A$_2$ are as described in formula I, Xb5 is halogen, and Yb1 can be a boron-derived functional group, such as for example B(OH)$_2$ or B(OR$_{b1}$)$_2$ wherein R$_{b1}$ can be a C$_1$-C$_4$ alkyl group or the two groups OR$_{b1}$ can form together with the boron atom a five membered ring, as for example a pinacol boronic ester, are reacted with compounds of formula XIV, wherein Xb6 is halogen, under Suzuki type conditions previously described, but also described in for example *Eu. J. of Org. Chem.*, 2014, 5901-5905 and *Bio. & Med. Chem. Letts.*, 2012 (23), 7268-7271, to give compounds of formula XV. Compounds of formula XV upon treatment with compounds of formula XVI, wherein Xb7 is halogen and R$_1$ is as described in formula I, in the presence of a palladium(II) catalyst, such as Pd(OAc)2, and an acetate source, for example sodium or potassium acetate, in an inert solvent such as toluene, xylene or DMA at temperatures between 50-180° C., leads to compounds of formula XVII. Such C—H activation protocols have been published in for example *Chemical Science*, 2013, 2374-2379 and *Ang. Chem. Int. Ed.*, 2007, 46, 7996-8000. Compounds of formula XVII can be treated with compounds of formula IX as described previously under scheme 3 to give compounds of formula Ic wherein R$_1$, A$_2$, R$_3$, R$_4$, are as described in formula I. Compounds of formula Ic wherein A$_2$, R$_1$, R$_2$, R$_3$ and R$_4$ are as described in formula I, can be oxidized to compounds of formula Id with reagents such as, for example a peracid as peracetic acid or m-chloroperbenzoic acid, or a hydroperoxide as for example hydrogen peroxide or tert-butylhydroperoxide, or an inorganic oxidant, like a mono-peroxodisulfate salt or potassium permanganate, preferentially meta-chloroperbenzoic acid.

For preparing all other compounds of the formula (I) functionalized according to the definitions of formula I, there are a large number of suitable known standard methods, for example alkylation, halogenation, acylation, amidation, oximation, oxidation and reduction, the choice of the preparation methods which are suitable depending on the properties (reactivity) of the substituents in the intermediates.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an) other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture. Depending on the procedure or the reaction conditions, the compounds of formula I, which have salt-forming properties, can be obtained in free form or in the form of salts.

The compounds of formula I and, where appropriate, the tautomer's thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and herein below, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from *J. Med. Chem.* 1989, 32, 2561 or WO 2000/15615.1t is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 36 below can be prepared according to the methods described above. The examples which follow are intended to illustrate the invention and show preferred compounds of formula I. "Ph" represents the phenyl group. Free radicals represent methyl groups.

TABLE X

This table discloses the 18 substituent designations X.001 to X.018 for the formula (Iaa), (Iab), (Iac), (Iad), (Iaf), (Iag), (Iah) and (Iai) which are disclosed after Table X.

| Comp. No | Zx |
|---|---|
| X.001 | CF$_3$ |
| X.002 | H |
| X.003 | 3-fluorophenyl |
| X.004 | 4-fluorophenyl |
| X.005 | 4-(trifluoromethyl)phenyl |
| X.006 | 3,5-difluorophenyl |
| X.007 | 4-(trifluoromethyl)phenyl |
| X.008 | 1-cyanocyclopropyl |
| X.009 | cyclopropyl |
| X.010 | 3,5-difluoropyridin-2-yl |
| X.011 | 1-(trifluoromethyl)cyclopropyl |
| X.012 | 2-(trifluoromethyl)styryl |
| X.013 | 3,5-difluoropyridin-2-yl |
| X.014 | 4-chloro-1-methylpyrazol-? |
| X.015 | 4-(trifluoromethyl)pyridin-2-yl |
| X.016 | pyrimidin-2-yl |
| X.017 | 3-(trifluoromethyl)-1-methylpyrazol-? |
| X.018 | 3-chloro-1-methylpyrazol-? |

The arrow denotes the point of attachment of the substituent to the ring.

Table 1:

This table discloses the 18 compounds 1.001 to 1.018 of the formula (Iaa):

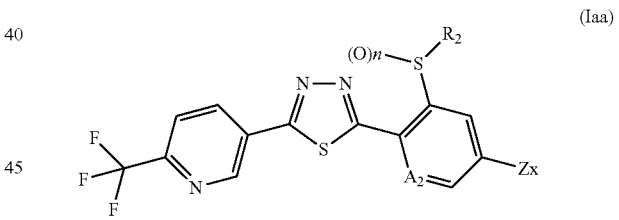

(Iaa)

wherein n is 0, R$_2$ is ethyl, A$_2$ is methine, and Zx is as defined in lines X.001-X.018 in table X. For example, compound 1.001 has the following structure:

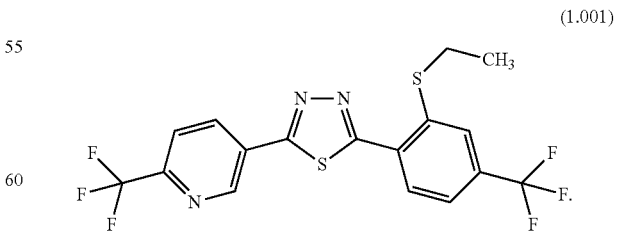

(1.001)

Table 2:

This table discloses the 18 compounds 2.001 to 2.018 of the formula (Iaa) wherein n is 2, R$_2$ is ethyl, A$_2$ is methine, and Zx is as defined in lines X.001-X.018 in table X.

Table 3:

This table discloses the 18 compounds 3.001 to 3.018 of the formula (Iaa) wherein n is 0, $R_2$ is ethyl, $A_2$ is nitrogen, and Zx is as defined in lines X.001-X.018 in table X.

Table 4:

This table discloses the 18 compounds 4.001 to 4.018 of the formula (Iaa) wherein n is 2, $R_2$ is ethyl, $A_2$ is nitrogen, and Zx is as defined in lines X.001-X.018 in table X.

Table 5:

This table discloses the 18 compounds 5.001 to 5.018 of the formula (Iab):

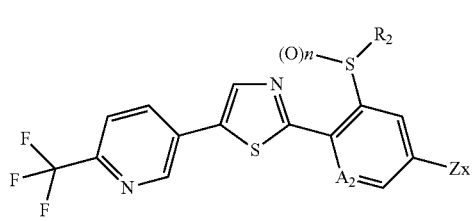

(Iab)

wherein n is 0, $R_2$ is ethyl, $A_2$ is methine, and Zx is as defined in lines X.001-X.018 in table X.

Table 6:

This table discloses the 18 compounds 6.001 to 6.018 of the formula (Iab) wherein n is 2, $R_2$ is ethyl, $A_2$ is methine, and Zx is as defined in lines X.001-X.018 in table X.

Table 7:

This table discloses the 18 compounds 7.001 to 7.018 of the formula (Iab) wherein n is 0, $R_2$ is ethyl, $A_2$ is nitrogen, and Zx is as defined in lines X.001-X.018 in table X.

Table 8:

This table discloses the 18 compounds 8.001 to 8.018 of the formula (Iab) wherein n is 2, $R_2$ is ethyl, $A_2$ is nitrogen, and Zx is as defined in lines X.001-X.018 in table X.

Table 9:

This table discloses the 18 compounds 9.001 to 9.018 of the formula (Iac):

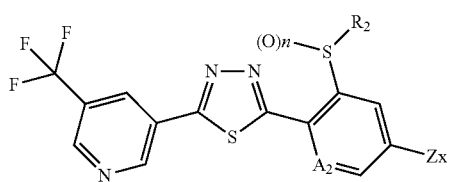

(Iac)

wherein n is 0, $R_2$ is ethyl, $A_2$ is methine, and Zx is as defined in lines X.001-X.018 in table X.

Table 10:

This table discloses the 18 compounds 10.001 to 10.018 of the formula (Iac) wherein n is 2, $R_2$ is ethyl, $A_2$ is methine, and Zx is as defined in lines X.001-X.018 in table X.

Table 11:

This table discloses the 18 compounds 11.001 to 11.018 of the formula (Iac) wherein n is 0, $R_2$ is ethyl, $A_2$ is nitrogen, and Zx is as defined in lines X.001-X.018 in table X.

Table 12:

This table discloses the 18 compounds 12.001 to 12.018 of the formula (Iac) wherein n is 2, $R_2$ is ethyl, $A_2$ is nitrogen, and Zx is as defined in lines X.001-X.018 in table X.

Table 13:

This table discloses the 18 compounds 13.001 to 13.018 of the formula (Iad):

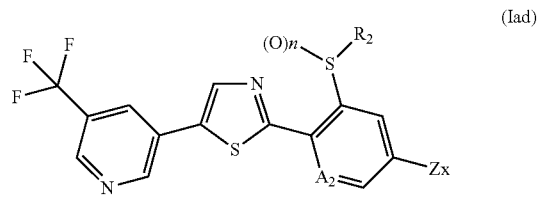

(Iad)

wherein n is 0, $R_2$ is ethyl, $A_2$ is methine, and Zx is as defined in lines X.001-X.018 in table X.

Table 14:

This table discloses the 18 compounds 14.001 to 14.018 of the formula (Iad) wherein n is 2, $R_2$ is ethyl, $A_2$ is methine, and Zx is as defined in lines X.001-X.018 in table X.

Table 15:

This table discloses the 18 compounds 15.001 to 15.018 of the formula (Iad) wherein n is 0, $R_2$ is ethyl, $A_2$ is nitrogen, and Zx is as defined in lines X.001-X.018 in table X.

Table 16:

This table discloses the 18 compounds 16.001 to 16.018 of the formula (Iad) wherein n is 2, $R_2$ is ethyl, $A_2$ is nitrogen, and Zx is as defined in lines X.001-X.018 in table X.

Table 17:

This table discloses the 18 compounds 17.001 to 17.018 of the formula (Iae):

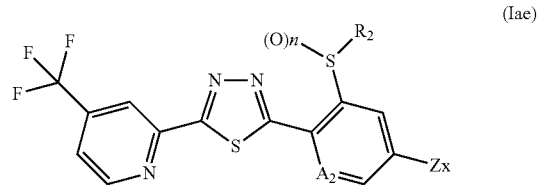

(Iae)

wherein n is 0, $R_2$ is ethyl, $A_2$ is methine, and Zx is as defined in lines X.001-X.018 in table X.

Table 18:

This table discloses the 18 compounds 18.001 to 18.018 of the formula (Iae) wherein n is 2, $R_2$ is ethyl, $A_2$ is methine, and Zx is as defined in lines X.001-X.018 in table X.

Table 19:

This table discloses the 18 compounds 19.001 to 19.018 of the formula (Iae) wherein n is 0, $R_2$ is ethyl, $A_2$ is nitrogen, and Zx is as defined in lines X.001-X.018 in table X.

Table 20:

This table discloses the 18 compounds 20.001 to 20.018 of the formula (Iae) wherein n is 2, $R_2$ is ethyl, $A_2$ is nitrogen, and Zx is as defined in lines X.001-X.018 in table X.

Table 21:

This table discloses the 18 compounds 21.001 to 21.018 of the formula (Iaf):

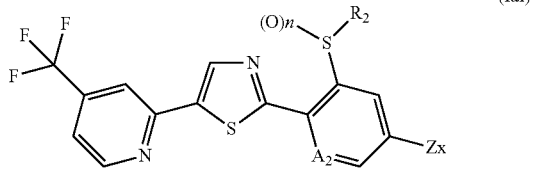

wherein n is 0, $R_2$ is ethyl, $A_2$ is methine, and Zx is as defined in lines X.001-X.018 in table X.

Table 22:

This table discloses the 18 compounds 22.001 to 22.018 of the formula (Iaf) wherein n is 2, $R_2$ is ethyl, $A_2$ is methine, and Zx is as defined in lines X.001-X.018 in table X.

Table 23:

This table discloses the 18 compounds 23.001 to 23.018 of the formula (Iaf) wherein n is 0, $R_2$ is ethyl, $A_2$ is nitrogen, and Zx is as defined in lines X.001-X.018 in table X.

Table 24:

This table discloses the 18 compounds 24.001 to 24.018 of the formula (Iaf) wherein n is 2, $R_2$ is ethyl, $A_2$ is nitrogen, and Zx is as defined in lines X.001-X.018 in table X.

Table 25:

This table discloses the 18 compounds 25.001 to 25.018 of the formula (Iag):

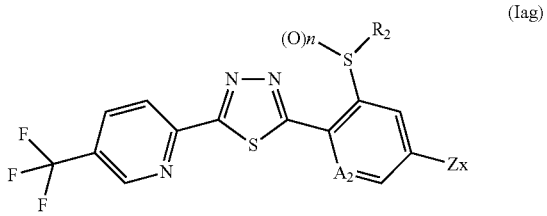

wherein n is 0, $R_2$ is ethyl, $A_2$ is methine, and Zx is as defined in lines X.001-X.018 in table X.

Table 26:

This table discloses the 18 compounds 26.001 to 26.018 of the formula (Iag) wherein n is 2, $R_2$ is ethyl, $A_2$ is methine, and Zx is as defined in lines X.001-X.018 in table X.

Table 27:

This table discloses the 18 compounds 27.001 to 27.018 of the formula (Iag) wherein n is 0, $R_2$ is ethyl, $A_2$ is nitrogen, and Zx is as defined in lines X.001-X.018 in table X.

Table 28:

This table discloses the 18 compounds 28.001 to 28.018 of the formula (Iag) wherein n is 2, $R_2$ is ethyl, $A_2$ is nitrogen, and Zx is as defined in lines X.001-X.018 in table X.

Table 29:

This table discloses the 18 compounds 29.001 to 29.018 of the formula (Iah):

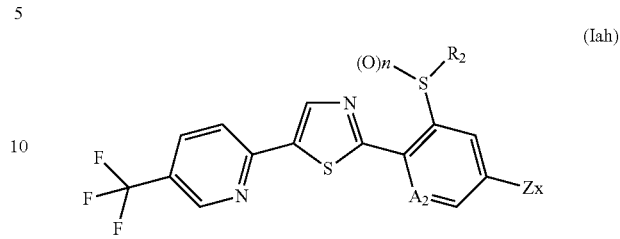

wherein n is 0, $R_2$ is ethyl, $A_2$ is methine, and Zx is as defined in lines X.001-X.018 in table X.

Table 30:

This table discloses the 18 compounds 30.001 to 30.018 of the formula (Iah) wherein n is 2, $R_2$ is ethyl, $A_2$ is methine, and Zx is as defined in lines X.001-X.018 in table X.

Table 31:

This table discloses the 18 compounds 31.001 to 31.018 of the formula (Iah) wherein n is 0, $R_2$ is ethyl, $A_2$ is nitrogen, and Zx is as defined in lines X.001-X.018 in table X.

Table 32:

This table discloses the 18 compounds 32.001 to 32.018 of the formula (Iah) wherein n is 2, $R_2$ is ethyl, $A_2$ is nitrogen, and Zx is as defined in lines X.001-X.018 in table X.

Table 33:

This table discloses the 18 compounds 33.001 to 33.018 of the formula (Iai)

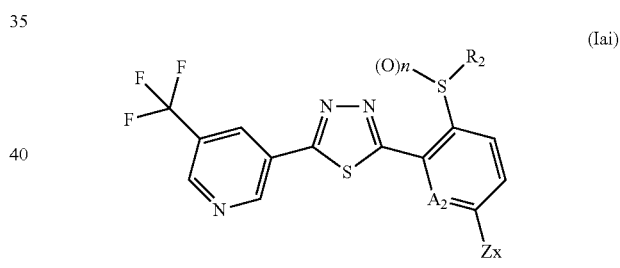

wherein n is 0, $R_2$ is ethyl, $A_2$ is nitrogen, and Zx is as defined in lines X.001-X.018 in table X. For example, compound 33.016 has the following structure:

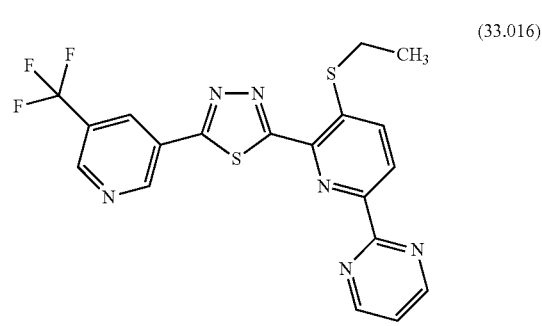 [SMILES: CCSc1ccc(-c2ncccn2)nc1-c1nnc(-c2cncc(C(F)(F)F)c2)s1]

Table 34:

This table discloses the 18 compounds 34.001 to 34.018 of the formula (Iai) wherein n is 2, $R_2$ is ethyl, $A_2$ is nitrogen, and Zx is as defined in lines X.001-X.018 in table X.

The compounds of formula I according to the invention are preventively and/or curatively valuable active ingredients in the field of pest control, even at low rates of application, which have a very favourable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate.

Examples of the abovementioned animal pests are:

from the order Acarina, for example,

*Acalitus* spp, *Aculus* spp, *Acaricalus* spp, *Aceria* spp, *Acarus siro, Amblyomma* spp., *Argas* spp., *Boophilus* spp., *Brevipalpus* spp., *Bryobia* spp, *Calipitrimerus* spp., *Chorioptes* spp., *Dermanyssus gallinae, Dermatophagoides* spp., *Eotetranychus* spp, *Eriophyes* spp., *Hem itarsonemus* spp, *Hyalomma* spp., *Ixodes* spp., *Olygonychus* spp, *Ornithodoros* spp., *Polyphagotarsone latus, Panonychus* spp., *Phyllocoptruta oleivora, Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale, Anomala orientalis, Anthonomus* spp., *Aphodius* spp, *Astylus atromaculatus, Ataenius* spp, *Atomaria linearis, Chaetocnema tibialis, Cerotoma* spp, *Conoderus* spp, *Cosmopolites* spp., *Cotinis nitida, Curculio* spp., *Cyclocephala* spp, *Dermestes* spp., *Diabrotica* spp., *Diloboderus abderus, Epilachna* spp., *Eremnus* spp., *Heteronychus arator, Hypothenemus hampei, Lagria vilosa, Leptinotarsa decemLineata, Lissorhoptrus* spp., *Liogenys* spp, *Maecolaspis* spp, *Maladera castanea, Megascelis* spp, *Melighetes aeneus, Melolontha* spp., *Myochrous armatus, Orycaephilus* spp., *Otiorhynchus* spp., *Phyllophaga* spp, *Phlyctinus* spp., *Popillia* spp., *Psylliodes* spp., *Rhyssomatus aubtil is, Rhizopertha* spp., *Scarabeidae, Sitophilus* spp., *Sitotroga* spp., *Somaticus* spp, *Sphenophorus* spp, *Sternechus subsignatus, Tenebrio* spp., *Tribolium* spp. and *Trogoderma* spp.;

from the order Diptera, for example,

*Aedes* spp., *Anopheles* spp, *Antherigona soccata, Bactrocea pleas, Bibio hortulanus, Bradysia* spp, *Calliphora erythrocephala, Ceratitis* spp., *Chrysomyia* spp., *Culex* spp., *Cuterebra* spp., *Dacus* spp., *Delia* spp, *Drosophila melanogaster, Fannia* spp., *Gastrophilus* spp., *Geomyza tripunctata, Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis* spp, *Rivelia quadrifasciata, Scatella* spp, *Sciara* spp., *Stomoxys* spp., *Tabanus* spp., *Tannia* spp. and *Tipula* spp.;

from the order Hemiptera, for example,

*Acanthocoris scabrator, Acrosternum* spp, *Adelphocoris lineolatus, Amblypelta nitida, Bathycoelia thalassina, Blissus* spp, *Cimex* spp., *Clavigralla tomentosicollis, Creontiades* spp, *Distantiella theobroma, Dichelops furcatus, Dysdercus* spp., *Edessa* spp, *Euchistus* spp., *Eurydema pulchrum, Eurygaster* spp., *Halyomorpha halys, Horcias nobilellus, Leptocorisa* spp., *Lygus* spp, *Margarodes* spp, *Murgantia histrionic, Neomegalotomus* spp, *Nesidiocoris tenuis, Nezara* spp., *Nysius simulans, Oebalus insularis, Piesma* spp., *Piezodorus* spp, *Rhodnius* spp., *Sahlbergella singularis, Scaptocoris castanea, Scotino-phara* spp., *Thyanta* spp, *Triatoma* spp., *Vatiga illudens;*

*Acyrthosium pisum, Adalges* spp, *Agalliana ensigera, Agonoscena targionii, Aleurodicus* spp, *Aleurocanthus* spp, *Aleurolobus barodensis, Aleurothrixus floccosus, Aleyrodes brassicae, Amarasca biguttula, Amritodus atkinsoni, Aonidiella* spp., *Aphididae, Aphis* spp., *Aspidiotus* spp., *Aulacorthum solani, Bactericera cockerelli, Bemisia* spp, *Brachycaudus* spp, *Brevicoryne brassicae, Cacopsylla* spp, *Cavariella aegopodii Scop., Ceroplaster* spp., *Chrysomphalus aonidium, Chrysomphalus dictyospermi, Cicadella* spp., *Cofana spectra, Cryptomyzus* spp, *Cicadulina* spp, *Coccus hesperidum, Dalbulus maidis, Dialeurodes* spp, *Diaphorina citri, Diuraphis noxia, Dysaphis* spp, *Empoasca* spp., *Eriosoma larigerum, Erythroneura* spp., *Gascardia* spp., *Glycaspis brimblecombei, Hyadaphis pseudobrassicae, Hyalopterus* spp, *Hyperomyzus pallidus, Idioscopus clypealis, Jacobiasca lybica, Laodelphax* spp., *Lecanium corni, Lepidosaphes* spp., *Lopaphis erysimi, Lyogenys maidis, Macrosiphum* spp., *Mahanarva* spp, *Metcalfa pruinosa, Metopolophium dirhodum, Myndus crudus, Myzus* spp., *Neotoxoptera* sp, *Nephotettix* spp., *Nilaparvata* spp., *Nippolachnus piri Mats, Odonaspis ruthae, Oregma lanigera Zehnter, Parabemisia myricae, Paratrioza cockerelli, Parlatoria* spp., *Pemphigus* spp., *Peregrinus maidis, Perkinsiella* spp, *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;* from the order Hymenoptera, for example,

*Acromyrmex, Arge* spp, *Atta* spp., *Cephus* spp., *Diprion* spp., *Diprionidae, Gilpinia polytoma, Hoplocampa* spp., *Lasius* spp., *Monomorium pharaonis, Neodiprion* spp., *Pogonomyrmex* spp, *Slenopsis invicta, Solenopsis* spp. and *Vespa* spp.;

from the order Isoptera, for example,

*Coptotermes* spp, *Corniternes cumulans, Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Gracholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp.,

*Lyonetia* spp., *Malacosoma* spp., *Mamestra brassicae*, *Manduca sexta*, *Mythimna* spp, *Noctua* spp, *Operophtera* spp., *Orniodes indica*, *Ostrinia nubilalis*, *Pammene* spp., *Pandemis* spp., *Panolis flammea*, *Papaipema nebris*, *Pectinophora gossypiela*, *Perileucoptera coffeella*, *Pseudaletia unipuncta*, *Phthorimaea operculella*, *Pieris rapae*, *Pieris* spp., *Plutella xylostella*, *Prays* spp., *Pseudoplusia* spp, *Rachiplusia nu*, *Richia albicosta*, *Scirpophaga* spp., *Sesamia* spp., *Sparganothis* spp., *Spodoptera* spp., *Sylepta derogate*, *Synanthedon* spp., *Thaumetopoea* spp., *Tortrix* spp., *Trichoplusia ni*, *Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae*, *Locusta* spp., *Neocurtilla hexadactyla*, *Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis*;

from the order Thysanoptera, for example,

*Calliothrips phaseoli*, *Frankliniella* spp., *Heliothrips* spp, *Hercinothrips* spp., *Parthenothrips* spp, *Scirtothrips aurantii*, *Sericothrips variabilis*, *Taeniothrips* spp., *Thrips* spp;

from the order Thysanura, for example, *Lepisma saccharina*.

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; *Lauraceae*, such as avocado, Cinnamonium or camphor; and also tobacco, nuts, coffee, eggplants, sugarcane, tea, pepper, grapevines, hops, the plantain family, latex plants and ornamentals.

The active ingredients according to the invention are especially suitable for controlling *Aphis craccivora*, *Diabrotica balteata*, *Heliothis virescens*, *Myzus persicae*, *Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

In a further aspect, the invention may also relate to a method of controlling damage to plant and parts thereof by plant parasitic nematodes (Endoparasitic-, Sem iendoparasitic- and Ectoparasitic nematodes), especially plant parasitic nematodes such as root knot nematodes, *Meloidogyne hapla*, *Meloidogyne incognita*, *Meloidogyne javanica*, *Meloidogyne arenaria* and other *Meloidogyne* species; cyst-forming nematodes, *Globodera rostochiensis* and other *Globodera* species; *Heterodera avenae*, *Heterodera glycines*, *Heterodera schachtii*, *Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor*, *Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus*, *Pratylenchus penetrans*, *Pratylenchus curvitatus*, *Pratylenchus goodeyi* and other *Pratylenchus* species; Burrowing nematodes, *Radopholus similis* and other *Radopholus* species; Reniform nematodes, *Rotylenchus robustus*, *Rotylenchus reniforrnis* and other *Rotylenchus* species; *Scutellonema* species; Stubby root nematodes, *Trichodorus prim itivus* and other *Trichodorus* species, *Paratrichodorus* species; Stunt nematodes, *Tylenchorhynchus claytoni*, *Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; Anon (*A. ater*, *A. circumscriptus*, *A. hortensis*, *A. rufus*); Bradybaenidae (*Bradybaena fruticum*); *Cepaea* (*C. hortensis*, *C. Nemoralis*); ochlodina; *Deroceras* (*D. agrestis*, *D. empiricorum*, *D. laeve*, *D. reticulatum*); *Discus* (*D. rotundatus*); *Euomphalia*; *Galba* (*G. trunculata*); *Helicelia* (*H. itala*, *H. obvia*); Helicidae *Helicigona arbustorum*); Helicodiscus; *Helix* (*H. aperta*); *Limax* (*L. cinereoniger*, *L. flavus*, *L. marginatus*, *L. maximus*, *L. tenellus*); *Lymnaea*; *Milax* (*M. gagates*, *M. marginatus*, *M. sowerbyi*); *Opeas*; *Pomacea* (*P. canaticulata*); *Vallonia* and *Zanitoides*.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as 6-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens*, *Xenorhabdus nematophilus*; toxins produced by animals, such as scorpion toxins, arachnid toxins, wasp toxins and other insect-specific neurotoxins; toxins produced by fungi, such as *Streptomycetes* toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch). The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Crops may also be modified for enhanced resistance to fungal (for example *Fusarium*, *Anthracnose*, or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store ambients and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.whoint/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/064072, WO2006/128870, EP 1724392, WO2005/113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against wood borers listed in the following tables A and B:

TABLE A

Examples of exotic woodborers of economic importance.

| Family | Species | Host or Crop Infested |
| --- | --- | --- |
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
| --- | --- | --- |
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |

TABLE B-continued

Examples of native woodborers of economic importance.

| Family | Species | Host or Crop Infested |
|---|---|---|
| Cerambycidae | Goes pulverulentus | Beech, Elm, Nuttall, Willow, Black oak, Cherrybark oak, Water oak, Sycamore |
|  | Goes tigrinus | Oak |
|  | Neoclytus acuminatus | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
|  | Neoptychodes trilineatus | Fig, Alder, Mulberry, Willow, Netleaf hackberry |
|  | Oberea ocellata | Sumac, Apple, Peach, Plum, Pear, Currant, Blackberry |
|  | Oberea tripunctata | Dogwood, *Viburnum*, Elm, Sourwood, Blueberry, *Rhododendron*, Azalea, Laurel, Poplar, Willow, Mulberry |
|  | Oncideres cingulata | Hickory, Pecan, Persimmon, Elm, Sourwood, Basswood, Honeylocust, Dogwood, Eucalyptus, Oak, Hackberry, Maple, Fruit trees |
|  | Saperda calcarata | Poplar |
|  | Strophiona nitens | Chestnut, Oak, Hickory, Walnut, Beech, Maple |
| Scolytidae | Corthylus columbianus | Maple, Oak, Yellow-poplar, Beech, Boxelder, Sycamore, Birch, Basswood, Chestnut, Elm |
|  | Dendroctonus frontalis | Pine |
|  | Dryocoetes betulae | Birch, Sweetgum, Wild cherry, Beech, Pear |
|  | Monarthrum fasciatum | Oak, Maple, Birch, Chestnut, Sweetgum, Blackgum, Poplar, Hickory, Mimosa, Apple, Peach, Pine |
|  | Phloeotribus liminaris | Peach, Cherry, Plum, Black cherry, Elm, Mulberry, Mountain-ash |
|  | Pseudopityophthorus pruinosus | Oak, American beech, Black cherry, Chickasaw plum, Chestnut, Maple, Hickory, Hornbeam, Hophornbeam |
| Sesiidae | Paranthrene simulans | Oak, American chestnut |
|  | Sannina uroceriformis | Persimmon |
|  | Synanthedon exitiosa | Peach, Plum, Nectarine, Cherry, Apricot, Almond, Black cherry |
|  | Synanthedon pictipes | Peach, Plum, Cherry, Beach, Black Cherry |
|  | Synanthedon rubrofascia | Tupelo |
|  | Synanthedon scitula | Dogwood, Pecan, Hickory, Oak, Chestnut, Beech, Birch, Black cherry, Elm, Mountain-ash, *Viburnum*, Willow, Apple, Loquat, Ninebark, Bayberry |
|  | Vitacea polistiformis | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass ataenius, *A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and green bugs.

The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *olenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis*, *Periplaneta americana*, *Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergatesspp.*, *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus*, *Chlorophorus pilosis*, *Anobium punctatum*, *Xestobium rufovillosum*, *Ptilinuspecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthesrugicollis*, *Xyleborus* spec., *Tryptodendron* spec., *Apate monachus*, *Bostrychus capucins*, *Heterobostrychus brunneus*, *Sinoxylon* spec. and *Dinoderus minutus*, and also hymenopterans such as *Sirex juvencus*, *Urocerus gigas*, *Urocerus gigas taignus* and *Urocerus augur*, and termites such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis* and *Coptotermes formosanus*, and bristletails such as *Lepisma saccharina*.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspo-emulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated. The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl-hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the *Compendium* of Herbicide Adjuvants, 10$^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 I/ha, especially from 10 to 1000 I/ha.

Preferred formulations can have the following compositions (weight %):

Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15&
solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

Suspension Concentrate

| | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

"Mp." means melting point in ° C. Free radicals represent methyl groups. $^1$H NMR and $^{19}$F NMR measurements were recorded on a Brucker 400 MHz spectrometer, chemical shifts are given in ppm relevant to a TMS standard. Spectra measured in deuterated solvents as indicated.

EtOAc is ethyl acetate, DCM is dichloromethane.

LCMS Methods:

Method 1:

Spectra were recorded on a Mass Spectrometer from Waters (SQD, SQDII or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 mm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH, gradient: 10-100% B in 1.2 min; Flow (mL/min) 0.85

Mass Spectroscopy Method ESI-MS

LC-20AD Mass Spectrometer from Shimadzu (Single quadrupole mass spectrometer)

Instrument Parameters:
Ionisation method: Electrospray
Polarity: positive and negative ions
Capillary (kV) 1.50
Cone (V) unknown
Extractor (V) 5.00
Source Temperature (° C.) 200
Desolvation Temperature (° C.) 250
Cone gas Flow (l/Hr) 90
Desolvation gas Flow (l/Hr) 90
Mass range: 50 to 1000 Da Example H1: 2-[3-ethylsulfonyl-5-(trifluoromethyl)-2-pyridyl]-5-([6-(trifluoromethyl)-3-pyridyl]-1,3,4-thiadiazole (Compound P21, Table P)

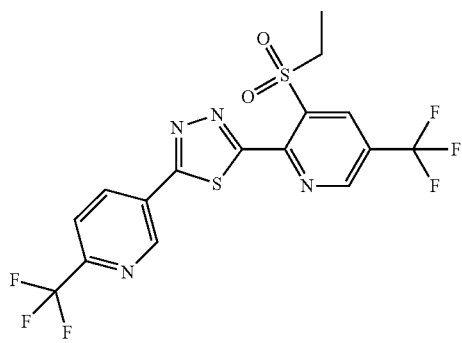 [SMILES: CCS(=O)(=O)c1cc(C(F)(F)F)cnc1-c1nnc(-c2ccc(C(F)(F)F)nc2)s1]

Step A: Preparation of ethyl 3-ethylsulfanyl-5-(trifluoromethyl)pyridine-2-carboxylate

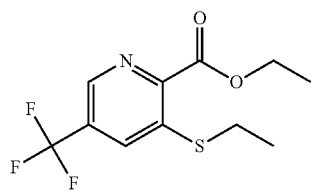 [SMILES: CCOC(=O)c1ncc(C(F)(F)F)cc1SCC]

To a solution of ethyl 3-chloro-5-(trifluoromethyl)pyridine-2-carboxylate (10 g, 39.6 mmol, commercial compound) in acetonitrile (100 mL) was added NaSEt (3.6 g, 43 mmol) at 0° C., The mixture was stirred at rt for 20 h. Then it was quenched with water, diluted with EtOAc, and the aqueous phase separated. The aqueous phase was back extracted with EtOAc (3 times) and the combined organic phases washed with brine, dried over Na$_2$SO$_4$, and concentrated in vacuo. The residue was purified by chromatography on silica, eluting with PE:EtOAc=10:1, to give the pure title compound as a yellow oil.

Step B: Preparation of ethyl 3-ethylsulfonyl-5-(trifluoromethyl)pyridine-2-carboxylate

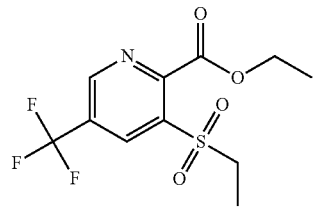 [SMILES: CCOC(=O)c1ncc(C(F)(F)F)cc1S(=O)(=O)CC]

To a solution of ethyl 3-ethylsulfanyl-5-(trifluoromethyl)pyridine-2-carboxylate (8.0 g, 28.7 mmol) in dichloromethane (100 mL) was added m-CPBA (13.5 g, 78.5 mmol). The reaction mixture was stirred at room temperature overnight. The mixture was then quenched with water (100 mL) and extracted with dichloromethane (3×50 mL). The combined organic phases were washed with saturated sodium bicarbonate solution and saturated sodium thiosulfate solution, dried over Na$_2$SO$_4$, and concentrated in vacuo. The residue was purified by chromatography on silica gel (eluting with PE:EtOAc=4:1) to give the pure title compound as a yellow oil.

Step C: Preparation of 3-ethylsulfonyl-5-(trifluoromethyl)pyridine-2-carbohydrazide

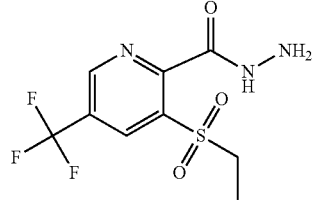 [SMILES: CCS(=O)(=O)c1cc(C(F)(F)F)cnc1C(=O)NN]

To a solution of ethyl 3-ethylsulfonyl-5-(trifluoromethyl)pyridine-2-carboxylate (500 mg, 1.6 mmol) in THF (10 mL) was added hydrazine hydrate (5 mL). The mixture was stirred at rt for 4 h. Then it was quenched with water, the aqueous phase was extracted with EtOAc (×3). The combined organic phases were washed with brine, dried over Na$_2$SO$_4$, and concentrated in vacuo to give the title compound as a yellow solid.

$^1$H NMR (400 MHz, DMSO-d$_6$): δ 9.97 (s, 1H), 9.32 (s, 1H), 8.55 (s, 1H), 4.61 (brs, 2H), 4.47 (s, 2H), 3.68 (q, 2H), 1.20 (t, 3H).

LCMS (method 1): 298 (M+H)$^+$; retention time: 0.63 min.
ESI-MS(+): 320 (M+Na); ESI-MS(−): 296 (M−H).

Step D: Preparation of 3-ethylsulfonyl-5-(trifluoromethyl)-N'-[6-(trifluoromethyl)pyridine-3-carbonyl]pyridine-2-carbohydrazide

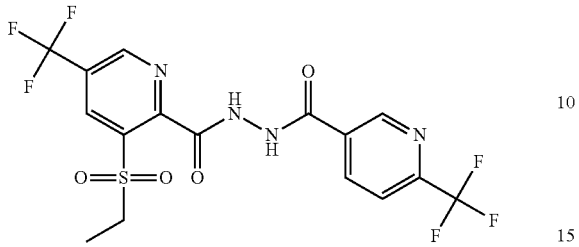

To a stirred solution of 6-(trifluoromethyl)pyridine-3-carboxylic acid (126 mg, 0.66 mmol, prepared as described in *Eu. J. Org. Chem.*, (8), 2003, 1559-1568) in dichloromethane (6 mL) was added oxalyl chloride (0.12 mL, 1.3 mmol) at 0° C., followed by catalytic DMF (0.01 mL). The mixture was stirred at 0° C. for 1 h and then the reaction mixture was concentrated in vacuo. The residue was dissolved in dichloromethane (5 mL) and added dropwise to a solution of 3-ethylsulfonyl-5-(trifluoromethyl)pyridine-2-carbohydrazide (180 mg, 0.6 mmol) and Et₃N (0.16 mL, 1.2 mmol) in dichloromethane (5 mL). The mixture was stirred at rt for 2 h and then concentrated in vacuo. The residue obtained and purified by column chromatography on silica gel (eluting with petroleum ether:EtOAc=3:1) to give the title compound as light yellow solid.

¹H NMR (400 MHz, DMSO-d₆): δ 11.30 (brs, 1H), 11.13 (brs, 1H), 9.45 (s, 1H), 9.21 (s, 1H), 8.65 (s, 1H), 8.63 (d, J=1.6 Hz, 1H), 8.10 (d, J=1.6 Hz, 1H), 3.01 (q, 2H), 1.20 (t, 3H).
ESI-MS(+): 493 (M+Na); ESI-MS(−): 469 (M−H).

Step E: 2-[3-ethylsulfonyl-5-(trifluoromethyl)-2-pyridyl]-5-[6-(trifluoromethyl)-3-pyridyl]-1,3,4-thiadiazole (Compound P21, Table P)

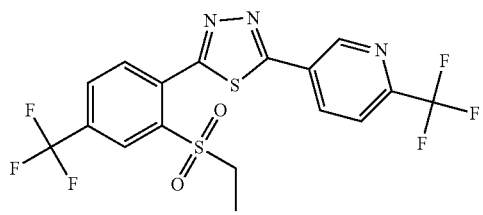 [SMILES: CCS(=O)(=O)c1cc(C(F)(F)F)ccc1-c1nnc(-c2ccc(C(F)(F)F)nc2)s1]

A solution of 3-ethylsulfonyl-5-(trifluoromethyl)-N'-[6-(trifluoromethyl)pyridine-3-carbonyl]pyridine-2-carbohydrazide (120 mg, 0.25 mmol) and Lawesson's reagent (120 mg, 0.29 mmol) in toluene (4 mL) was stirred at 110° C. overnight. The reaction mixture was then quenched with water, extracted with EtOAc (×3 mL). The combined organic layers were washed with brine (5 mL), and dried over anhydrous Na₂SO₄. After filtration and concentration in vacuo, a crude product was obtained that was purified by column chromatography on silica gel (eluting with petroleum ether:EtOAc=5:1) to afford the title compound as white solid. Mp 193-195° C.

¹H NMR (400 MHz, DMSO-d₆): δ 9.48-9.51 (m, 2H), 8.76-8.77 (m, 2H), 8.14-8.16 (m, 1H), 4.05 (q, 2H), 1.31 (t, 3H). ¹⁹F NMR (400 MHz, DMSO-d₆): δ-60.52 (s, 3F); −66.15 (s, 3F).

ESI-MS(+): 491 (M+Na); ESI-MS(−): 467 (M−H).
LCMS (method 1): 441 (M+H)⁺; retention time: 1.16 min.

Example H2: 2-[2-ethylsulfanyl-4-(trifluoromethyl)phenyl]-5-[6-(trifluoromethyl)-3-pyridyl]-1,3,4-thiadiazole (Compound P2, Table P)

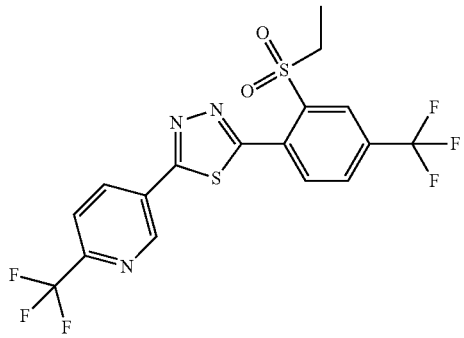 [SMILES: CCS(=O)(=O)c1cc(C(F)(F)F)ccc1-c1nnc(-c2ccc(C(F)(F)F)nc2)s1]

Step A: Preparation of 2-ethylsulfanyl-4-(trifluoromethyl)benzoic acid

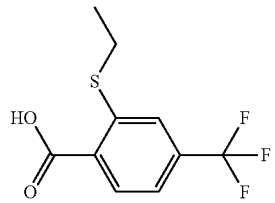 [SMILES: CCSc1cc(C(F)(F)F)ccc1C(=O)O]

To a solution of 2-chloro-4-(trifluoromethyl)benzoic acid (1.1 g, 5.0 mmol) in NMP (10 mL) was slowly added NaSEt (1.2 g, 14.3 mmol), The mixture was stirred at 120° C. for 24 h. It was then cooled to room temperature, quenched with water, and the aqueous phase was adjust to Ph<3 with 3N HCl. Then it was extracted with EtOAc (×3) and the combined organic phases were washed with brine, dried over Na₂SO₄, and concentrated in vacuo to yield the title compound as a as light yellow solid.

Step B: Preparation of ethyl 2-ethylsulfanyl-4-(trifluoromethyl)benzoate

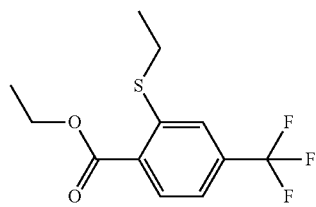 [SMILES: CCOC(=O)c1ccc(C(F)(F)F)cc1SCC]

To a solution of 2-ethylsulfanyl-4-(trifluoromethyl)benzoic acid (1.0 g, 4.0 mmol) in ethanol (10 mL) was dropwise added thionyl chloride (0.6 mL, 8.0 mmol). The mixture was refluxed overnight. Then it was evaporated to dryness to give the title compound as yellow solid.

Step C: Preparation of 2-ethylsulfanyl-4-(trifluoromethyl)benzohydrazide

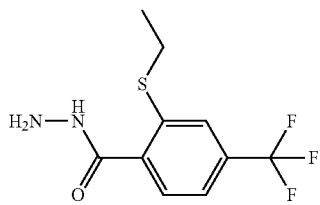 [SMILES: CCSc1cc(C(F)(F)F)ccc1C(=O)NN]

To a solution of compound ethyl 2-ethylsulfanyl-4-(trifluoromethyl)benzoate (0.9 g, 3.2 mmol) in THF (20 mL) was added hydrazine hydrate (10 mL). The mixture was stirred at rt for 4 h. Then it was quenched with water, and the aqueous phase was extracted with EtOAc (×3). The combined organic phases were washed with brine, dried over $Na_2SO_4$, and concentrated in vacuo to give the title compound as a yellow solid.

Step D: Preparation of N'-[2-ethylsulfanyl-4-(trifluoromethyl)benzoyl]-6-(trifluoromethyl)pyridine-3-carbohydrazide

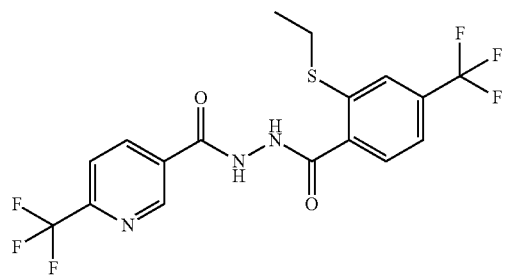 [SMILES: CCSc1cc(C(F)(F)F)ccc1C(=O)NNC(=O)c1ccc(C(F)(F)F)nc1]

A solution of 6-(trifluoromethyl)pyridine-3-carbonyl chloride (prepared as described in step D, example H1) in dichloromethane (5 mL) was added dropwise to a solution of 2-ethylsulfanyl-4-(trifluoromethyl)benzohydrazide (290 mg, 1.1 mmol), and $Et_3N$ (0.32 mL, 2.4 mmol) in dichloromethane (10 mL). The mixture was stirred at rt for 5 h and then evaporated to dryness. The residue obtained was purified with column chromatography on silica gel (eluting with petroleum ether:EtOAc=2:1) to give the title compound as a light yellow solid. $^1$H NMR (400 MHz, DMSO-$d_6$): δ 10.82 (brs, 2H), 9.21 (s, 1H), 8.52 (d, J=1.6 Hz, 1H), 8.10 (d, J=1.6 Hz, 1H), 7.60-7.71 (m, 3H), 3.05 (q, 2H), 1.21 (t, 3H).

ESI-MS(+):460 (M+Na); ESI-MS(−): 436 (M−H).

Step E: 2-[2-ethylsulfanyl-4-(trifluoromethyl)phenyl]-5-[6-(trifluoromethyl)-3-pyridyl]-1,3,4-thiadiazole (Compound P2, Table P)

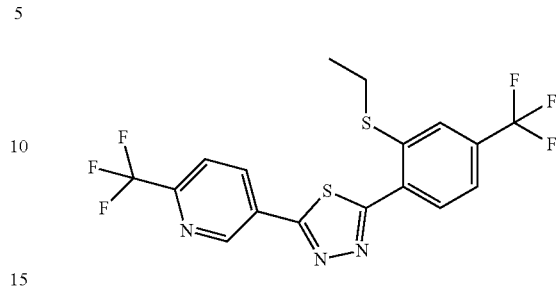

A solution of N'-[2-ethylsulfanyl-4-(trifluoromethyl)benzoyl]-6-(trifluoromethyl)pyridine-3-carbohydrazide (35 mg, 0.8 mmol) and Lawesson's reagent (60 mg, 0.88 mmol) in toluene (4 mL) was stirred at 110° C. overnight. Then, it was quenched with water, extracted with EtOAc (×3) and the combined organic phases were collected and washed with brine (5 mL), dried over anhydrous $Na_2SO_4$, filtered and concentrated in vacuo. The crude product so obtained was purified by column chromatography on silica gel (eluting with petroleum ether:EtOAc=4:1) to afford the title compound as a yellow solid, Mp 170-172° C.

$^1$H NMR (400 MHz, DMSO-$d_6$): δ 9.43 (s, 1H), 8.75 (d, 1H), 8.27 (d, 1H), 8.13 (d, 1H), 7.91 (s, 1H), 7.79 (d, 1H), 3.17 (q, 2H), 1.23 (t, 3H).

ESI-MS(+): 436 (M+H).

LCMS (method 1): 436 (M+H)$^+$; retention time: 1.24 min.

Example H3: Preparation of 2-[2-ethylsulfonyl-4-(trifluoromethyl)phenyl]-5-[6-(trifluoromethyl)-3-pyridyl]-1,3,4-thiadiazole (Compound P1, Table P)

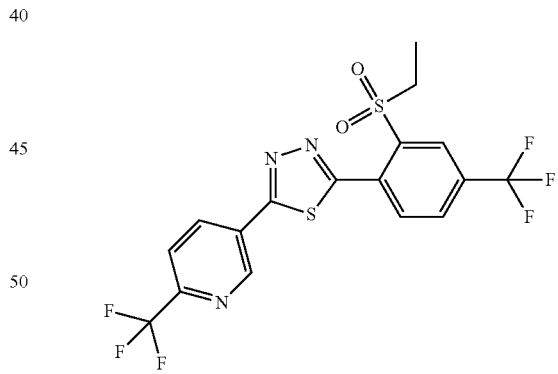

To a solution of: 2-[2-ethylsulfanyl-4-(trifluoromethyl)phenyl]-5-[6-(trifluoromethyl)-3-pyridyl]-1,3,4-thiadiazole (50 mg, 0.11 mmol) in dichloromethane (2 mL) was added m-CPBA (38 mg, 0.22 mmol). The reaction mixture was stirred at room temperature overnight. The mixture was then quenched with water (10 mL) and extracted with dichloromethane (×3). The combined organic phases were washed with saturated sodium bicarbonate solution and saturated sodium thiosulfate solution, dried over $Na_2SO_4$, and evaporated to dryness. The residue was purified by chromatography on silica (eluting with PE:EtOAc=4:1) to give the title compound as a white solid. Mp 154-156° C.

$^1$H NMR (400 MHz, DMSO-d$_6$): δ 9.45 (s, 1H), 8.75 (d, 1H), 8.37 (d, 1H), 8.35 (s, 1H), 8.15 (d, 2H), 3.70 (q, 2H), 1.22 (t, 3H). $^{19}$F NMR (400 MHz, DMSO-d$_6$): δ-61.05 (s, 3F); −66.05 (s, 3F).

ESI-MS(+):490 (M+Na); ESI-MS(−): 466 (M−H).

LCMS (method 1): 468 (M+H)$^+$; retention time: 1.06 min.

Example H4: 2-[2-ethylsulfanyl-4-(trifluoromethyl)phenyl]-5-[6-(trifluoromethyl)-3-pyridyl]thiazole (Compound P7, Table P)

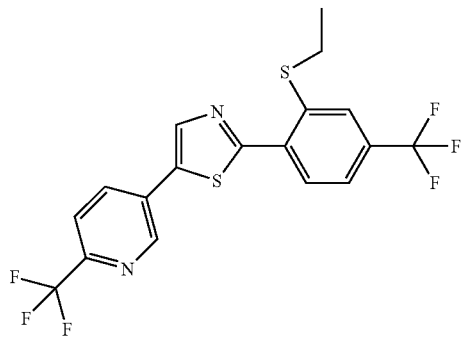 [SMILES: CCSc1cc(C(F)(F)F)ccc1-c1ncc(-c2ccc(C(F)(F)F)nc2)s1]

Step A: Preparation of 2-[2-chloro-4-(trifluoromethyl)phenyl]thiazole

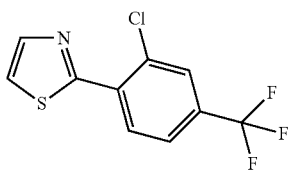 [SMILES: FC(F)(F)c1ccc(-c2nccs2)c(Cl)c1]

A mixture of [2-chloro-4-(trifluoromethyl)phenyl]boronic acid (270 mg, 1.2 mmol), Pd(PPh$_3$)$_4$ (60 mg, 0.05 mmol), 2-Bromothiazole (160 mg, 1.0 mmol), and 2 N sodium bicarbonate aqueous solution (1.0 mL), in dioxane (5 mL) was refluxed overnight under N$_2$ atmosphere. Then it was quenched with water, extracted with EtOAc (×3). The combined organic layers were pooled and washed with brine (5 mL), dried over anhydrous Na$_2$SO$_4$, filtrated and concentrated in vacuo. The crude product was purified by column chromatography on silica gel (eluting with petroleum ether:EtOAc=20:1) to afford the title compound as a yellow solid.

$^1$H NMR (400 MHz, DMSO-d$_6$): δ 8.42 (d, 1H), 8.10 (s, 1H), 8.05 (d, 2H), 7.85 (d, 1H).

ESI-MS(+): 264 (M+H).

Step B: Preparation of 2-[2-chloro-4-(trifluoromethyl)phenyl]-5-[6-(trifluoromethyl)-3-pyridyl]thiazole

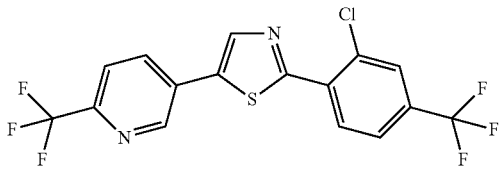 [SMILES: FC(F)(F)c1ccc(-c2ncc(-c3ccc(C(F)(F)F)nc3)s2)c(Cl)c1]

A mixture of 2-[2-chloro-4-(trifluoromethyl)phenyl]thiazole (1.7 g, 6.5 mmol), Pd(OAc)$_2$ (50 mg, 0.2 mmol), 5-bromo-2-(trifluoromethyl)pyridine (750 mg, 3.3 mmol), CH$_3$COOK (2.5 g, 6.5 mmol), in DMA (20 mL) was stirred at 100° C. overnight under a N$_2$ atmosphere. The reaction mixtures was quenched with water, and extracted with EtOAc (×3). The combined organic layers were collected and washed with brine (50 mL), dried over anhydrous Na$_2$SO$_4$, filtered and concentrated in vacuo. The crude product was purified by column chromatography on silica gel (eluting with petroleum ether:EtOAc=10:1) to afford the title compound as a solid.

$^1$H NMR (400 MHz, DMSO-d$_6$): δ 9.20 (s, 1H), 8.76 (S, 1H), 8.41-8.50 (m, 2H), 8.11 (s, 1H), 7.98 (d, 1H), 7.88 (d, 1H).

ESI-MS(+):409 (M+H).

Step C: Preparation of 2-[2-elhylsulfanyl-4-(trifluoromethyl)phenyl]-5-[6-(trifluoromethyl)-3-pyridyl]thiazole (Compound P7, Table P)

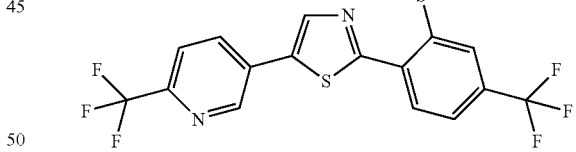

To a solution of 2-[2-chloro-4-(trifluoromethyl)phenyl]-5-[6-(trifluoromethyl)-3-pyridyl]thiazole (100 mg, 0.24 mmol) in NMP (2 mL) was added NaSEt (42 mg, 0.48 mmol), the mixture was stirred at 100° C. overnight. Then it was cooled to room temperature, quenched with water, and extracted with EtOAc (×3). The combined organic layers were collected and washed with brine (20 mL), dried over anhydrous Na$_2$SO$_4$, filtered and concentrated in vacuo. The crude product was purified with column chromatography on silica gel (eluting with petroleum ether:EtOAc=10:1) to afford the title compound as a solid. Mp. 118-120° C.

$^1$H NMR (400 MHz, DMSO-d$_6$): δ 9.20 (s, 1H), 9.70 (S, 1H), 8.44 (d, 1H), 8.24 (d, 1H), 7.98 (d, 1H), 7.80 (s, 1H), 7.68 (d, 1H), 3.13 (q, 2H), 1.24 (t, 3H).

ESI-MS(+):435 (M+H).

LCMS (method 1): 435(M+H)⁺; retention time: 1.29 min.

Example H5: Preparation of 2-[2-ethylsulfonyl-4-(trifluoromethyl)phenyl]-5-[6-(trifluoromethyl)-3-pyridyl]thiazole ((Compound P8, Table P)

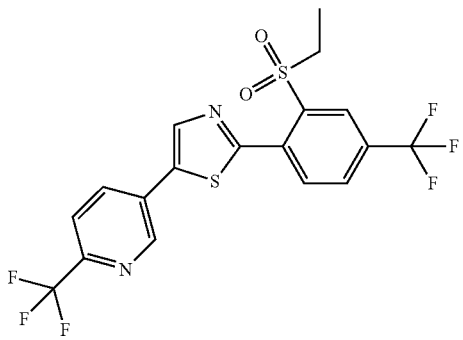

To a solution of 2-[2-ethylsulfanyl-4-(trifluoromethyl)phenyl]-5-[6-(trifluoromethyl)-3-pyridyl]thiazole (230 mg, 0.5 mmol) in DCM (5 mL) was added m-CPBA (240 mg, 1.0 mmol). The reaction mixture was stirred at room temperature overnight. The reaction mixture was quenched with water (10 mL) and then extracted with dichloromethane. The combined organic phases were washed with saturated sodium bicarbonate solution and saturated sodium thiosulfate solution, dried over $Na_2SO_4$, and concentrated in vacuo. The residue was purified by chromatography on silica (eluting with PE:EtOAc=5:1) to give the title compound as a white solid. Mp 159-161° C.

$^1$H NMR (400 MHz, DMSO-$d_6$): δ 9.21 (s, 1H), 8.71 (s, 1H), 8.47 (d, 1H), 8.32 (s, 1H), 8.31 (d, 1H), 8.10 (d, 1H), 8.03 (d, 1H), 3.82 (q, 2H), 1.21 (t, 3H). $^{19}$F NMR (400 MHz, DMSO-$d_6$): δ-61.03 (s, 3F); −65.83 (s, 3F). ESI-MS(+):466 (M+H); 489 (M+Na).

LCMS (method 1): 467(M+H)⁺; retention time: 1.11 min.

TABLE P

Examples of compounds prepared of formula (I)

| Entry | STRUCTURE | RT (min) | [M + H] (Mes.) | Method | Mp ° C. |
|---|---|---|---|---|---|
| P1 | 2-[2-ethylsulfonyl-4-(trifluoromethyl)phenyl]-5-[6-(trifluoromethyl)-3-pyridyl]-1,3,4-thiadiazole | 1.06 | 468 | 1 | 154-156 |
| P2 | 2-[2-ethylsulfanyl-4-(trifluoromethyl)phenyl]-5-[6-(trifluoromethyl)-3-pyridyl]-1,3,4-thiadiazole | 1.24 | 436 | 1 | 170-172 |
| P3 | 2-[2-ethylsulfanyl-4-(trifluoromethyl)phenyl]-5-[5-(trifluoromethyl)-3-pyridyl]-1,3,4-thiadiazole | 1.23 | 436 | 1 | 143-145 |
| P4 | 2-[2-ethylsulfonyl-4-(trifluoromethyl)phenyl]-5-[5-(trifluoromethyl)-3-pyridyl]-1,3,4-thiadiazole | 1.04 | 468 | 1 | 161-163 |
| P5 | 2-[3-ethylsulfanyl-5-(trifluoromethyl)-2-pyridyl]-5-[5-(trifluoromethyl)-3-pyridyl]-1,3,4-thiadiazole | 1.21 | 437 | 1 | 151-153 |
| P6 | 2-[3-ethylsulfonyl-5-(trifluoromethyl)-2-pyridyl]-5-[5-(trifluoromethyl)-3-pyridyl]-1,3,4-thiadiazole | 1.06 | 469 | 1 | 152-154 |
| P7 | 2-[2-ethylsulfanyl-4-(trifluoromethyl)phenyl]-5-[6-(trifluoromethyl)-3-pyridyl]thiazole | 1.29 | 435 | 1 | 118-120 |
| P8 | 2-[2-ethylsulfonyl-4-(trifluoromethyl)phenyl]-5-[6-(trifluoromethyl)-3-pyridyl]thiazole | 1.11 | 467 | 1 | 159-161 |
| P9 | 2-[2-ethylsulfonyl-4-(trifluoromethyl)phenyl]-5-[5-(trifluoromethyl)-3-pyridyl]thiazole | 1.12 | 467 | 1 | 194-196 |
| P10 | 2-[3-ethylsulfonyl-5-(trifluoromethyl)-2-pyridyl]-5-[4-(trifluoromethyl)-2-pyridyl]-1,3,4-thiadiazole | 1.17 | 469 | 1 | 191-195 |
| P11 | 2-[3-ethylsulfonyl-5-(trifluoromethyl)-2-pyridyl]thiazole | 1.00 | 323 | 1 | 110-112 |
| P12 | 2-[3-ethylsulfonyl-5-(trifluoromethyl)-2-pyridyl]-5-[4-(trifluoromethyl)-2-pyridyl]thiazole | 1.22 | 468 | 1 | 173-175 |
| P13 | 2-[3-ethylsulfonyl-5-(trifluoromethyl)-2-pyridyl]-5-[5-(trifluoromethyl)-2-pyridyl]thiazole | 1.17 | 468 | 1 | 208-210 |
| P14 | 2-[3-ethylsulfonyl-5-(trifluoromethyl)-2-pyridyl]-5-[5-(trifluoromethyl)-3-pyridyl]thiazole | 1.11 | 468 | 1 | 133-135 |
| P15 | 2-[3-ethylsulfonyl-5-(trifluoromethyl)-2-pyridyl]-5-[6-(trifluoromethyl)-3-pyridyl]thiazole | 1.12 | 468 | 1 | 228-230 |
| P16 | 2-(3-ethylsulfonyl-5-pyrimidin-2-yl-2-pyridyl)-5-[5-(trifluoromethyl)-3-pyridyl]-1,3,4-thiadiazole | 1.07 | 479 | 1 | 237-239 |
| P17 | 2-(3-ethylsulfonyl-6-pyrimidin-2-yl-2-pyridyl)-5-[5-(trifluoromethyl)-3-pyridyl]-1,3,4-thiadiazole | 0.96 | 479 | 1 | 188-191 |
| P18 | 2-(5-cyclopropyl-3-ethylsulfonyl-2-pyridyl)-5-[4-(trifluoromethyl)-2-pyridyl]-1,3,4-thiadiazole | 1.16 | 441 | 1 | 202-204 |
| P19 | 2-(5-cyclopropyl-3-ethylsulfonyl-2-pyridyl)-5-[5-(trifluoromethyl)-3-pyridyl]-1,3,4-thiadiazole | 1.11 | 441 | 1 | 162-164 |
| P20 | 2-(6-cyclopropyl-3-ethylsulfonyl-2-pyridyl)-5-[5-(trifluoromethyl)-3-pyridyl]-1,3,4-thiadiazole | 1.10 | 441 | 1 | 131-131 |
| P21 | 2-[3-ethylsulfonyl-5-(trifluoromethyl)-2-pyridyl]-5-[6-(trifluoromethyl)-3-pyridyl]-1,3,4-thiadiazole | 1.16 | 441 | 1 | 193-195 |

In table P, Mp = Melting point, mea. = measured

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Tables 1 to 36 and P of the present invention"):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50,439 (development code) (125)+TX, chinomethionat (126)+TX, chlorbenside (959)+TX, chlordimeform (964)+TX, chlordimeforrn hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin 1(696)+TX, cinerin 11(696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dino-penton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, ometlioate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chlysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cue-lure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure Ill (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure B$_1$ (alternative name) (839)+TX, trimedlure B$_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy) ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cyperrnethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CON]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O- diethyl O-4-methyl-2-oxo-2H-chromen-7-yl phosphorothioate (IUPAC name) (1074)+TX, O,O-diethyl O-6-methyl-2-propylpyrim idin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene Ill (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, fluxametamide (WO 2007/026965)+TX, a molluscicide selected from the group of substances consisting of bis(tributyltin) oxide (IUPAC name) (913)+TX, bromoacetamide [CON]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, diclphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422) TX, methiocarb (530)+TX, pyridin-4-amine (IUPAC name) (23)+TX, thiram (804)+TX, +trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imiben-conazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-

30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticid in-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyrid inyl)-2H,11Hnaphtho[2,1-b]pyrano[3,4-e]pyran-4-yl]methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl) ethyl]phenyl]-1H-pyrazole-4-carboxamide [926914-55-8]+TX, and microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, Adoxophyes orana granulovirus (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (Bio-Safe®+TX, BioNem-WP®+TX, VOTiVO®)+TX, *Bacillus firmus* strain I-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. amyloliquefaciens strain FZB24 (Taegro®+TX, Rhizopro®)+TX, *Bacillus thuringiensis* Cry 2Ae+TX, *Bacillus thuringiensis* Cry1Ab+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD #32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer Beauveria®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus*

*humicola*+TX, *Cryptococcus infirmo-miniatus*+TX, *Cryptococcus laurentii*+TX, *Cryptophlebia leucotreta granulovirus* (Cryptex®)+TX, *Cupriavidus campinensis*+TX, *Cydia pomonella granulovirus* (CYD-X®)+TX, *Cydia pomonella granulovirus* (Madex®+TX, Madex Plus®+TX, Madex Max/Carpovirusine®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, *Enterobacteriaceae*+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, *Granulovirus* (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera nucleopolyhedrovirus* (Helicovex®)+TX, *Helicoverpa zea* nuclear polyhedrosis virus (Gemstar®)+TX, Isoflavone-formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* sp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, *Pseudomons fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis* nucleopolyhedrovirus (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum rifai* (Mycostar®)+TX, *Trichoderma harzianum* T-22 (Trianum-P®+TX, PlantShield HC®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansfi* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanfi* (Mycotal®+TX, Vertalec®)+TX, Vip3Aa20 (VlPtera®)+TX, *Virgibacillus marismortui*+TX, *Xanthomonas campestris* pv. *Poae* (Camperico®)+TX, *Xenorhabdus bovienii*+TX, *Xenorhabdus nematophilus*; and Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemba)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of *Labiatae* (Botania®)+TX, extracts of clove rosemary peppermint and thyme oil (Garden insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, *Pedaliaceae* oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, *Rutaceae* plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame pepperm int thyme and cinnamon extracts (EF 300®)+TX, mixture of clove rosemary and peppermint extract (EF 400®)+TX, mixture of clove peperrnint garlic oil and mint (Soil Shot®)+TX, kaolin (Screen®)+TX, storage glucam of brown algae (Laminarin®); and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC-LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, (E+TX,Z+TX,Z)-3+TX,8+TX,11 Tetradecatrienyl acetate+TX, (Z+TX,Z+TX, E)-7+TX,11+TX,13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; and Macrobials including: *Aphelinus abdominalis*+TX, *Aphidius ervi* (*Aphelinus*-System®)+TX, *Acerophagus papaya*+TX, *Adalia bipunctata* (Adalia-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius califomicus* (Amblyline®+TX, Spical®)+TX, *Amblyseius cucumeris* (Thripe&+TX, Bugline Cucumeris®)+TX, *Amblyseius fallacis* (Fallacis®)+TX, *Amblyseius swirskii* (Bugline Swirskii®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus* kamali+TX, *Anagyrus loecki*+TX, *Anagyrus pseudococci* (Citripar®)+TX, *Anicetus benefices*+TX, *Anisopteromalus calandrae*+TX, *Anthocoris nemoralis* (*Anthocoris*-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chlysoperla camea* (Chrysoline®)+TX, *Chrysoperla camea* (Chrysopa®)+TX, *Chlysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Dimine&)+TX, *Del/phastus catalinae* (Delphastus®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (DacDigline®+TX, Minex®)+TX, *Diversinervus* spp.+TX, *Encarsia citrina*+TX, *Encarsia formosa* (Encarsia Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+TX, *Eretmocerus eremicus* (Ercal®+TX, Eretline e®)+TX, *Eretmocerus eremicus* (Bemimix®)+TX, *Eretmocerus hayati*+TX, *Eretmocerus mundus* (Bernipar®+TX, Eretline m®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Laryanem®+TX, B-Green®+TX, NemAttack®+TX, Nematop®)+TX, *Heterorhabditis megidis* (Nemasys H®+TX, BioNem H®+TX, Exhibitline Hm®+TX, Laryanem-M®)+TX, *Hippodamia convergens*+TX, *Hypoaspis aculeifer* (Aculeifer-System®+TX, Entomite-A®)+TX, *Hypoaspis miles* (Hypoline m®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline c®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spaangia cameroni* (Biopar®)+TX, *Neodryinus typhlocybae*+TX, *Neoseiulus califomicus*+TX, *Neoseiu/us cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Online i®)+TX, *Orius laevigatus* (Thripor-L®+TX, Oriline I®)+TX, *Orius majusculus* (Online m®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffee*+TX, *Phytoseiulus macropilus*+TX, *Phytoseiulus persimilis* (Spidex®+TX, Phytoline p®)+TX, *Podisus maculiventris* (Podisus®)+TX, *Pseudacteon curvatus*+TX, *Pseudacteon obtusus*+TX, *Pseudacteon tricuspis*+TX, *Pseudaphycus maculipennis*+TX, *Pseudeptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanerre)+TX, *Steinernema feltiae* (NemaShield®+TX, Nemasys F®+TX, BioNem F®+TX, *Steinernema*-System®+TX, NemAttack®+TX, Nemaplus®+TX, Exhibitline Sf®+TX, Scia-rid®+TX, Entonerre)+TX, *Steinernema kraussei* (Nemasys L®+TX, BioNem L®+TX, Exhibitline Srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine b®)+TX, *Trichogramma brassicae* (Tricho-Strip®)+TX, *Trichogramma evanescens*+TX, *Trichogramma minutum*+

TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline d®)+TX, *Erwinia amylovora* (Harpin) (ProAct®+TX, Ni-HIB IT Gold CST®)+TX, Ferri-phosphate (Ferramol®)+TX, Funnel traps (Trapline y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline f®)+TX, *Microctonus hyperodae*+TX, *Mycoleptodiscus terrestris* (Des-X®)+TX, BioGain®+TX, Aminomite®+TX, Zenox®+TX, Pheromone trap (Thripline Ams®)+TX, potassium bicarbonate (MilStop®)+TX, potassium salts of fatty acids (Sanova®)+TX, potassium silicate solution (Sil-Matrix®)+TX, potassium iodide+potassiumthiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+b®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual-A World *Compendium*; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "*Compendium of Pesticide Common Names*", which is accessible on the internet [A. Wood; *Compendium of Pesticide Common Names*, Copyright© 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from Tables 1 to 36 and P with active ingredients described above comprises a compound selected from Tables 1 to 36 and P and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables 1 to 36 and P and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1 to 36 and P and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/ planting of the seeds.

BIOLOGICAL EXAMPLES

Example B1: Insecticidal Action Against
*Diabrotica Balteata* (Corn Root Worm)

Maize sprouts, placed on an agar layer in 24-well microtiter plates were treated with aqueous test solutions prepared from 10,000 ppm DMSO stock solutions by spraying. After drying, the plates were infested with L2 larvae (6 to 10 per well). The samples were assessed for mortality 4 days after infestation.

The following compounds resulted in at least 80% mortality at an application rate of 200 ppm: P1, P4, P6, P8, P9, P10, P16, P17, P18, P19, and P20

Example B2: Insecticidal Action Against *Myzus Persicae* (Green Peach Aphid)

Sunflower leaf discs were placed on agar in a 24-well microtiter plate and sprayed with aqueous test solutions prepared from 10,000 ppm DMSO stock solutions. After drying, the leaf discs were infested with an aphid population of mixed ages. The samples were assessed for mortality 6 days after infestation. The following compounds resulted in at least 80% mortality at an application rate of 200 ppm: P4 and P19

Example B3: Insecticidal Action Against *Plutella Xylostella* (Diamond Back Moth)

24-well microtiter plates with artificial diet were treated with aqueous test solutions prepared from 10,000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm:

P1, P4, P6, P7, P8, P17, P18, P19, and P20

Example B4: Insecticidal Action Against
*Spodoptera Littoralis* (Egyptian Cotton Leaf Worm)

Cotton leaf discs were placed on agar in 24-well microtiter plates and sprayed with aqueous test solutions prepared from 10,000 ppm DMSO stock solutions. After drying the leaf discs were infested with five L1 larvae. The samples were assessed for mortality, anti-feedant effect, and growth inhibition in comparison to untreated samples 3 days after infestation. Control of *Spodoptera littoralis* by a test sample is when at least one of mortality, anti-feedant effect, and growth inhibition is higher than the untreated sample. The following compounds resulted in at least 80% control at an application rate of 200 ppm:

P1, P4, P6, P8, P9, P10, P14, P18, P19, and P20

Example B5: Insecticidal Action Against
*Spodoptera Littoralis* (Egyptian Cotton Leaf Worm)

Test compounds were applied by pipette from 10,000 ppm DMSO stock solutions into 24-well plates and mixed with agar. Lettuce seeds were placed on the agar and the multi well plate was closed by another plate which contains also agar. After 7 days the roots have absorbed the compound and the lettuce has grown into the lid plate. The lettuce leafs were now cut off into the lid plate. *Spodoptera* eggs were pipetted through a plastic stencil on a humid gel blotting paper and the plate closed with it. The samples were assessed for mortality, anti-feedant effect and growth inhibition in comparison to untreated samples 6 days after infestation.

The following compound gave an effect of at least 80% in at least one of the three categories (mortality, anti-feedancy, or growth inhibition) at a test rate of 12.5 ppm: P4

The invention claimed is:

1. A compound of formula I

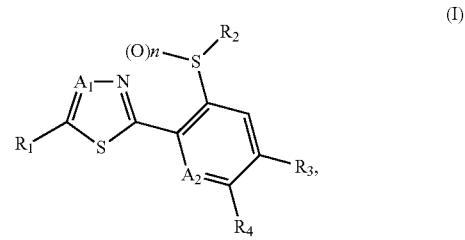

wherein
- $A_1$ is methine and $A_2$ is methine or N;
- $R_2$ is $C_1$-$C_4$alkyl, $C_3$-$C_4$cycloalkyl, or $C_1$-$C_4$alkyl-$C_3$-$C_4$-cycloalkyl;
- n is 0, 1 or 2;
- $R_1$ is selected from a group consisting of $J_0$ to $J_{30}$
J-0
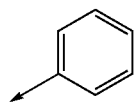
J-1
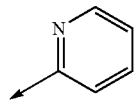
J-2
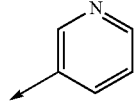
J-3
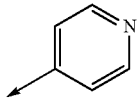
J-4
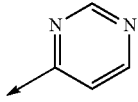
J-5
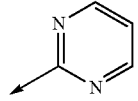
J-6
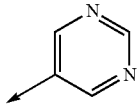
J-7
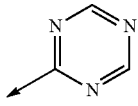
J-8
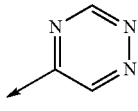
J-9
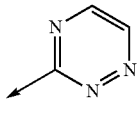
J-10
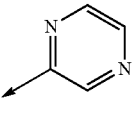
J-11
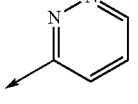
-continued
J-12
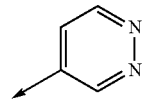
J-13
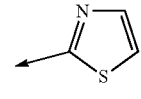
J-14
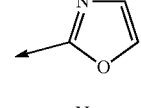
J-15
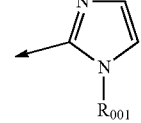
J-16
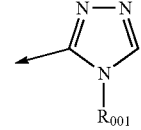
J-17
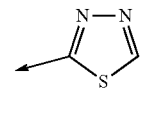
J-18
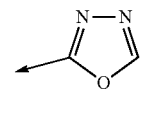
J-19
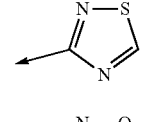
J-20
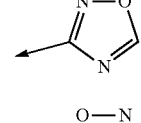
J-21
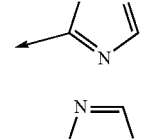
J-22
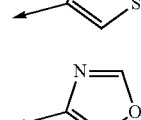
J-23
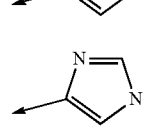
J-24
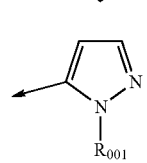
J-25

-continued

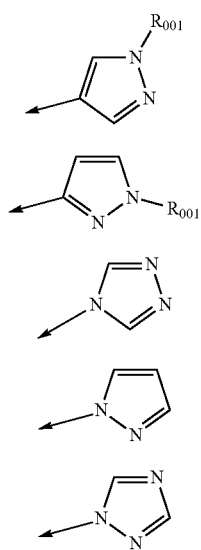

wherein the arrow represents the point of attachment to formula I, and each of the groups $J_0$ to $J_{30}$ can be mono- di- or trisubstituted by a group Rx, wherein Rx is independently selected from the group consisting of halogen cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, —C(O)$C_1$-$C_4$haloalkyl, $C_1$-$C_4$haloalkylsulfanyl, $C_1$-$C_4$haloalkylsulfinyl and $C_1$-$C_4$haloalkylsulfonyl, and wherein $R_{001}$ represents hydrogen or $C_1$-$C_4$alkyl;

$R_3$ and $R_4$, independently from each other, are hydrogen, halogen, $C_1$-$C_4$haloalkoxy, $C_1$-$C_4$haloalkyl, amino, hydroxy or cyano; or $R_3$ and $R_4$, independently from each other, are phenyl which can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or $R_3$ and $R_4$, independently from each other, are a five- to ten-membered monocyclic or fused bicyclic ring system linked via a carbon atom to the ring which contains the group $A_2$, said ring system can be aromatic, partially saturated or fully saturated and contains 1 to 4 hetero atoms selected from the group consisting of nitrogen, oxygen and sulfur, with the proviso that each ring system cannot contain more than 2 oxygen atoms or more than 2 sulfur atoms, said five- to ten-membered ring system can be mono- to polysubstituted by substituents independently selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or $R_3$ and $R_4$, independently from each other, are a five- to six-membered, aromatic, partially saturated or fully saturated ring system containing 1, 2 or 3 heteroatoms selected from the group consisting of nitrogen, oxygen and sulfur with the proviso that said ring system cannot contain more than one oxygen atom or more than one sulfur atom and linked via a nitrogen atom to the ring which contains the group $A_2$, said ring system can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or $R_3$ and $R_4$, independently from each other, are $C_3$-$C_6$cycloalkyl, or $C_3$-$C_6$cycloalkyl mono- or polysubstituted by substituents selected from the group consisting of halogen, cyano, $C_1$-$C_4$alkyl, $C_1$-$C_4$haloalkyl, $C_3$-$C_6$cycloalkyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$halo-alkylsulfinyl, $C_1$-$C_4$haloalkylsulfonyl and —C(O)$C_1$-$C_4$haloalkyl; or $R_3$ and $R_4$, independently from each other, are $C_2$-$C_6$alkenyl, or $C_2$-$C_6$alkenyl mono- or polysubstituted by substituents selected from the group consisting of halogen, cyano, $C_1$-$C_4$alkyl, $C_1$-$C_4$haloalkyl, $C_3$-$C_6$cycloalkyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or $R_3$ and $R_4$, independently from each other, are $C_2$-$C_6$alkynyl or $C_2$-$C_6$alkynyl mono- or polysubstituted by substituents selected from the group consisting of halogen, cyano, $C_1$-$C_4$alkyl, $C_1$-$C_4$haloalkyl, $C_3$-$C_6$cycloalkyl, tri($C_1$-$C_4$alkyl)silyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$halo-alkylsulfanyl, $C_1$-$C_4$haloalkylsulfinyl, $C_1$-$C_4$haloalkyl sulfonyl and —C(O)$C_1$-$C_4$haloalkyl; or $R_3$ and $R_4$, independently from each other, are $C_1$-$C_6$alkyl, or $C_1$-$C_6$alkyl mono- or polysubstituted by substituents selected from the group consisting of halogen, cyano, $C_1$-$C_4$alkyl, $C_1$-$C_4$haloalkyl, $C_3$-$C_6$cycloalkyl, tri($C_1$-$C_4$alkyl)silyl and phenyl, wherein said phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$halo-alkylsulfanyl, $C_1$-$C_4$haloalkylsulfinyl, $C_1$-$C_4$haloalkylsulfonyl and —C(O)$C_1$-$C_4$haloalkyl; and agrochemically acceptable salts, stereoisomers, enantiomers, tautomers of the compounds of formula I.

2. The compound of formula I according to claim 1, wherein
R$_3$ and R$_4$, independently from each other, are hydrogen, C$_1$-C$_4$haloalkyl, halogen or selected from a group consisting of Z-0 to Z-50:
Z-0
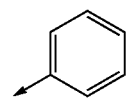
Z-1
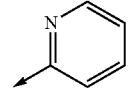
Z-2
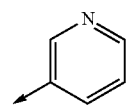
Z-3
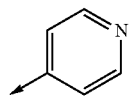
Z-4
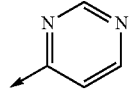
Z-5
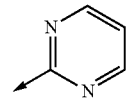
Z-6
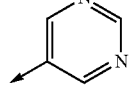
Z-7
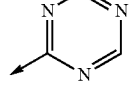
Z-8
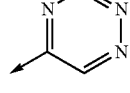
Z-9
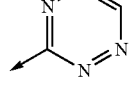
Z-10
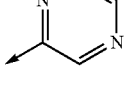
Z-11
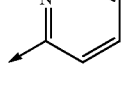
Z-12
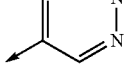
-continued
Z-13
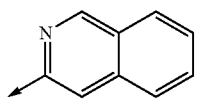
Z-14
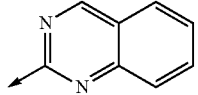
Z-15
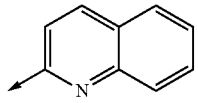
Z-16
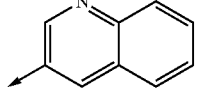
Z-17
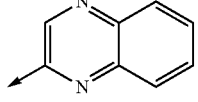
Z-18
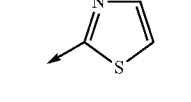
Z-19
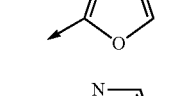
Z-20
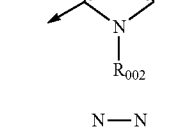
Z-21
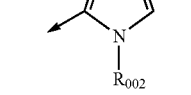
Z-22
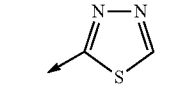
Z-23
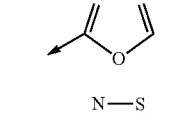
Z-24
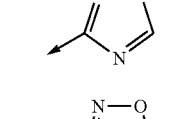
Z-25
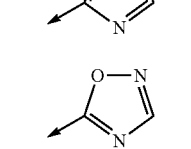
Z-26

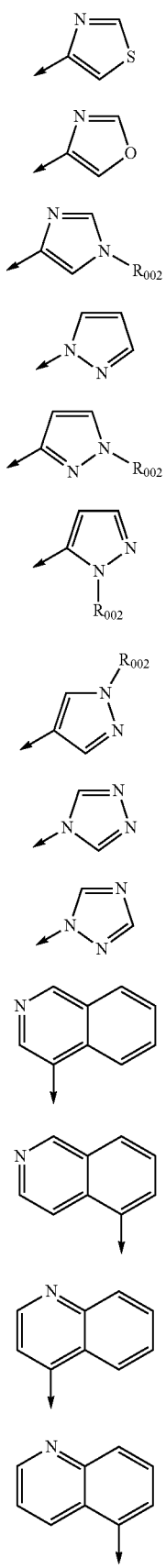
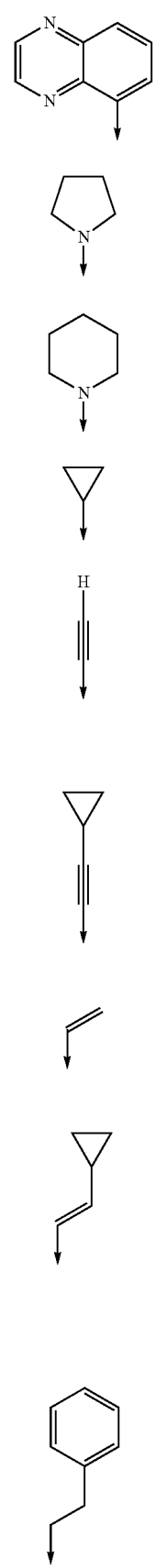

-continued

Z-49
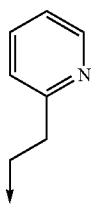

Z-50
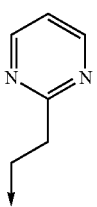

wherein each group Z-0 to Z-50 is mono- di- or trisubstituted with Rx; wherein each Rx is, independently selected from the group consisting of hydrogen, halogen, cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; and $R_{002}$ represents hydrogen or $C_1$-$C_4$haloalkyl.

3. The compound of formula I according to claim 1, represented by the compounds of formula I-3

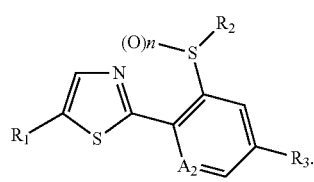
(I-3)

4. The compound of formula I according to claim 1, represented by the compounds of formula I-4

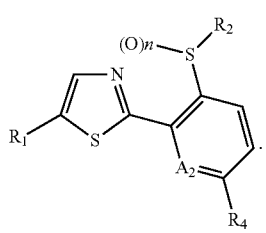
(I-4)

5. The compound of formula I according to claim 1, wherein
$R_1$ is pyridine which is monosubstituted by $C_1$-$C_4$haloalkyl;
$R_2$ is $C_1$-$C_4$alkyl;
$R_3$ is hydrogen, $C_1$-$C_4$haloalkyl, $C_1$-$C_6$cycloalkyl or pyrimidinyl;
$R_4$ is hydrogen, $C_1$-$C_4$haloalkyl, $C_1$-$C_6$cycloalkyl or pyrimidinyl;
n is 2.

6. The compound of formula I according to claim 1, wherein $R_x$ is selected from cyano, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, —C(O)$C_1$-$C_4$haloalkyl, $C_1$-$C_4$haloalkylsulfanyl, $C_1$-$C_4$haloalkylsulfinyl and $C_1$-$C_4$haloalkylsulfonyl.

7. The compound of formula I according to claim 1, wherein n is 2.

8. The compound of formula I according to claim 1, wherein $R_1$ is selected from the group consisting of $J_0$ and $J_2$-$J_{30}$.

9. The compound of formula I according to claim 1, wherein $R_1$ is $J_1$ and $R_x$ is selected from cyano, $C_1$-$C_4$alkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl, —C(O)$C_1$-$C_4$alkyl, —C(O)$C_1$-$C_4$haloalkyl, $C_1$-$C_4$haloalkylsulfanyl, $C_1$-$C_4$haloalkylsulfinyl and $C_1$-$C_4$haloalkylsulfonyl.

10. The compound of formula I according to claim 1, wherein at least one of $R_3$ and $R_4$ is not hydrogen.

11. The compound of formula I according to claim 10, wherein each of the groups $J_0$ to $J_{30}$ is mono- di- or trisubstituted by a group Rx.

12. A pesticidal composition, which comprises at least one compound of formula I according to claim 1 or, where appropriate, a tautomer thereof, in each case in free form or in agrochemically utilizable salt form, as active ingredient and at least one auxiliary.

13. A method for controlling pests, which comprises applying a composition according to claim 12 to the pests or their environment with the exception of a method for treatment of the human or animal body by surgery or therapy and diagnostic methods practised on the human or animal body.

14. A method for the protection of plant propagation material from the attack by pests, which comprises treating the propagation material or the site, where the propagation material is planted, with a composition according to claim 12.

15. A plant propagation material treated with a compound according to claim 1.

16. A compound selected from the group consisting of
2-[2-ethylsulfanyl-4-(trifluoromethyl)phenyl]-5-[6-(trifluoromethyl)-3-pyridyl]thiazole;
2-[2-ethylsulfonyl-4-(trifluoromethyl)phenyl]-5-[6-(trifluoromethyl)-3-pyridyl]thiazole;
2-[2-ethylsulfonyl-4-(trifluoromethyl)phenyl]-5-[5-(trifluoromethyl)-3-pyridyl]thiazole;
2-[3-ethylsulfonyl-5-(trifluoromethyl)-2-pyridyl]-5-[4-(trifluoromethyl)-2-pyridyl]thiazole;
2-[3-ethyl sulfonyl-5-(trifluoromethyl)-2-pyridyl]-5-[5-(trifluoromethyl)-2-pyridyl]thiazole;
2-[3-ethylsulfonyl-5-(trifluoromethyl)-2-pyridyl]-5-[5-(trifluoromethyl)-3-pyridyl]thiazole; and
2-[3-ethylsulfonyl-5-(trifluoromethyl)-2-pyridyl]-5-[6-(trifluoromethyl)-3-pyridyl]thiazole.

* * * * *